(12) United States Patent
Chatterji et al.

(10) Patent No.: US 9,669,042 B2
(45) Date of Patent: *Jun. 6, 2017

(54) COMPOSITIONS AND FORMULATIONS OF GLUCOSAMINE FOR TRANSDERMAL AND TRANSMUCOSAL ADMINISTRATION

(71) Applicant: Vital Medicine, LLC, Princeton, NJ (US)

(72) Inventors: Anjan Chatterji, New York, NY (US); Grant Cooper, Princeton, NJ (US); David Schwartz, Morristown, NJ (US)

(73) Assignee: Vital Medicine, LLC, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/662,062

(22) Filed: Mar. 18, 2015

(65) Prior Publication Data

US 2015/0283156 A1 Oct. 8, 2015

Related U.S. Application Data

(63) Continuation of application No. 13/797,163, filed on Mar. 12, 2013, now Pat. No. 9,012,430.

(60) Provisional application No. 61/675,272, filed on Jul. 24, 2012.

(51) Int. Cl.
| | | |
|---|---|---|
| *A01N 43/04* | (2006.01) |
| *A61K 31/70* | (2006.01) |
| *A61K 31/7008* | (2006.01) |
| *A61K 9/00* | (2006.01) |
| *A61K 45/06* | (2006.01) |
| *A61K 31/726* | (2006.01) |
| *A61K 31/715* | (2006.01) |
| *A61K 31/10* | (2006.01) |
| *A61K 31/737* | (2006.01) |
| *A61K 33/06* | (2006.01) |
| *A61K 33/14* | (2006.01) |
| *A61H 35/00* | (2006.01) |
| *A61H 33/04* | (2006.01) |

(52) U.S. Cl.
CPC ........ *A61K 31/7008* (2013.01); *A61K 9/0014* (2013.01); *A61K 31/10* (2013.01); *A61K 31/715* (2013.01); *A61K 31/726* (2013.01); *A61K 31/737* (2013.01); *A61K 33/06* (2013.01); *A61K 33/14* (2013.01); *A61K 45/06* (2013.01); *A61H 35/00* (2013.01); *A61H 2033/048* (2013.01)

(58) Field of Classification Search
None
See application file for complete search history.

(56) References Cited

U.S. PATENT DOCUMENTS

| | | |
|---|---|---|
| 5,958,462 A | 9/1999 | McLean |
| 6,399,093 B1 | 6/2002 | Petrus |
| 7,803,787 B2 | 9/2010 | Marcum et al. |
| 9,012,430 B2 | 4/2015 | Chatterji et al. |
| 2003/0180389 A1 | 9/2003 | Phillips |
| 2005/0232980 A1* | 10/2005 | Chen ............ A61K 31/045 424/448 |
| 2005/0277617 A1* | 12/2005 | Fukuda ............ A23G 4/10 514/53 |
| 2007/0020218 A1 | 1/2007 | Richardson |

FOREIGN PATENT DOCUMENTS

| | | |
|---|---|---|
| JP | 2004-307452 | 11/2004 |
| JP | 2004-331636 A | 11/2004 |
| KR | 10-2007-0109778 A | 11/2007 |

OTHER PUBLICATIONS

Cohen et al., "A Randomized, Double-Blind, Placebo Controlled Trial of a Topical Cream Containing Glucosamine Sulfate, Chondroitin Sulfate, and Camphor for Osteoarthritis of the Knee", Journal of Rheumatology. (3) Mar. 30, 2003, pp. 523-528.
International Preliminary Report on Patentability for PCT Application No. PCT/US2013/051570 dated Feb. 5, 2015.
International Search Report and Written Opinion for PCT Application No. PCT/US2013/051570 dated Oct. 15, 2013.
Messier et al., "Glucosamine/Chondroitin Combined with Exercise for the Treatment of Knee Osteoarthritis: a Preliminary Study," OsteoArthritis and Cartilage,(2007), 15(11), pp. 1256-1266.

* cited by examiner

*Primary Examiner* — Patrick Lewis
(74) *Attorney, Agent, or Firm* — Stanley D. Liang; Liang, Frank & King LLP

(57) ABSTRACT

Disclosed are compositions and formulations comprising glucosamine or a pharmaceutically acceptable salt thereof for use in the treatment of joint conditions and adapted for use in a bath or soak or bath beads, powders, salts, and oils, kits, and methods of treatment using the same. Also disclosed are lozenges, suppositories, patches, and topical creams comprising glucosamine or a pharmaceutically acceptable salt thereof for use in the treatment of joint conditions and methods of treatment using the same. In some embodiments the joint conditions include osteoarthritis.

12 Claims, 8 Drawing Sheets

COMPOSITIONS AND FORMULATIONS OF GLUCOSAMINE FOR TRANSDERMAL AND TRANSMUCOSAL ADMINISTRATION

CROSS-REFERENCE TO RELATED PATENT APPLICATIONS

This application is a continuation of U.S. application Ser. No. 13/797,163, filed Mar. 12, 2013, now U.S. Pat. No. 9,012,430 issued on Apr. 21, 2015, which claims priority to U.S. Provisional Patent Application No. 61/675,272, filed Jul. 24, 2012, the entire contents of which are incorporated herein by reference in their entirety.

BACKGROUND OF THE INVENTION

Joint conditions and the pain and disability associated with joint conditions affect millions of individuals. One such joint condition is arthritis, which involves inflammation of one or more joints. Osteoarthritis, in particular, affects 27 million Americans. This number is expected to increase as the median age in the U.S. continues to rise. Osteoarthritis, also known as degenerative arthritis or degenerative joint disease, is a group of mechanical abnormalities involving degradation of joints, including articular cartilage and subchondral bone. In some cases, symptoms include, for example, joint pain, tenderness, stiffness, locking, and the presence of increased intra-articular fluid.

SUMMARY OF THE INVENTION

Current medical strategies for treating osteoarthritis include pharmaceutical therapy (such as oral administration of acetaminophen, non-steroidal anti-inflammatory drugs (NSAIDs), and narcotics or administration of steroid or joint lubrication injections), physical and occupational therapy, prescription of medical devices (such as splints, braces, and shoe inserts), and surgery including joint realignment surgery (osteotomy) and joint replacement surgery (arthroplasty).

Oral administration of the monosaccharide amino sugar glucosamine, which is a constituent of hyaluronic acid, has been shown in some studies to have mild to moderate efficacy in the treatment of joint conditions such as osteoarthritis. Prior oral glucosamine treatments however have been limited by the fact that glucosamine is well absorbed orally, but undergoes substantial first-pass metabolism. First-pass metabolism (also known as presystemic metabolism) is a phenomenon of drug metabolism whereby the concentration of a drug is greatly reduced as it passes through the liver before it reaches the systemic circulation. The liver metabolizes many drugs; sometimes to such an extent that only a small amount of active drug emerges from the liver to the rest of the circulatory system. The first pass through the liver greatly reduces the bioavailability of glucosamine.

Advantages of the baths, soaks, lozenges, suppositories, patches, and topical creams comprising glucosamine or a pharmaceutically acceptable salt thereof, compositions adapted therefor, and methods of treatment using the same described herein include, but are not limited to, avoiding first-pass metabolism by allowing glucosamine and other substances to be absorbed directly into the systemic circulation. Further advantages include providing new and expanded transdermal and transmucosal treatment options for patients suffering from joint conditions, including osteoarthritis.

In one aspect, disclosed herein are compositions for use in the treatment of osteoarthritis, the composition comprising glucosamine or a pharmaceutically acceptable salt thereof, the composition adapted for use in a bath or soak. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the glucosamine or a pharmaceutically acceptable salt thereof is greater than 25% by weight of the composition. In further embodiments, the glucosamine or a pharmaceutically acceptable salt thereof is greater than 50% by weight of the composition. In still further embodiments, the glucosamine or a pharmaceutically acceptable salt thereof is greater than 75% by weight of the composition. In some embodiments, the glucosamine or a pharmaceutically acceptable salt thereof is less than 75% by weight of the composition. In further embodiments, the glucosamine or a pharmaceutically acceptable salt thereof is less than 50% by weight of the composition. In still further embodiments, the glucosamine or a pharmaceutically acceptable salt thereof is less than 25% by weight of the composition. In some embodiments, the composition further comprises chondroitin sulfate. In some embodiments, the composition further comprises methylsulfonylmethane. In some embodiments, the composition further comprises a transdermal permeation enhancer. In further embodiments, the composition further comprises the transdermal permeation enhancer promotes transdermal penetration of the glucosamine. In still further embodiments, the composition further comprises the transdermal permeation enhancer comprises one or more selected from the group comprising: sea salt, urea, a sulphoxide, an azone, an oxazolidinone, a pyrrolidone, a fatty alcohol, a fatty acid ester, a fatty acid, a fatty alcohol ether, a surfactant, an essential oil, a terpene, and a terpenoid. In some embodiments, the composition further comprises one or more selected from the group consisting of: sodium chloride, magnesium chloride, potassium chloride, and magnesium sulfate.

In another aspect, disclosed herein are bath beads for use in the treatment of osteoarthritis, the bath bead comprising glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the bath bead further comprises chondroitin sulfate. In some embodiments, the bath bead further comprises methylsulfonylmethane.

In another aspect, disclosed herein are bath powders for use in the treatment of osteoarthritis, the bath powder comprising glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the bath powder further comprises chondroitin sulfate. In some embodiments, the bath powder further comprises methylsulfonylmethane.

In another aspect, disclosed herein are bath salts for use in the treatment of osteoarthritis, the bath salt comprising glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the bath salt further comprises chondroitin sulfate. In some embodiments, the bath salt further comprises methylsulfonylmethane.

In another aspect, disclosed herein are bath oils for use in the treatment of osteoarthritis, the bath oil comprising glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the bath oil further comprises chondroitin sulfate. In some embodiments, the bath oil further comprises methylsulfonylmethane.

In another aspect, disclosed herein are kits for use in the treatment of osteoarthritis, the kit adapted for creating a bath or soak, the kit comprising about 500 g to about 3000 g of glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the kit further comprises chondroitin sulfate. In some embodiments, the kit further comprises methylsulfonylmethane.

In another aspect, disclosed herein are methods of making a composition for use in the treatment of osteoarthritis, the composition adapted for use in a bath or soak, the method comprising the step of combining glucosamine or a pharmaceutically acceptable salt thereof and a transdermal permeation enhancer. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the transdermal permeation enhancer comprises one or more selected from the group consisting of: sea salt, urea, a sulphoxide, an azone, an oxazolidinone, a pyrrolidone, a fatty alcohol, a fatty acid ester, a fatty acid, a fatty alcohol ether, a surfactant, an essential oil, a terpene, and a terpenoid. In further embodiments, the transdermal permeation enhancer is sea salt. In some embodiments, the glucosamine or a pharmaceutically acceptable salt thereof and the transdermal permeation enhancer is further combined with chondroitin sulfate. In some embodiments, the glucosamine or a pharmaceutically acceptable salt thereof and the transdermal permeation enhancer is further combined with methylsulfonylmethane. In some embodiments, the glucosamine or a pharmaceutically acceptable salt thereof and the transdermal permeation enhancer is further combined with one or more selected from the group consisting of: sodium chloride, magnesium chloride, potassium chloride, and magnesium sulfate. In some embodiments, the method results in a unit dose comprising about 500 g to about 3000 g of glucosamine or a pharmaceutically acceptable salt thereof.

In another aspect, disclosed herein are formulations for use in the treatment of osteoarthritis, the formulation comprising: glucosamine or a pharmaceutically acceptable salt thereof and a pharmaceutically acceptable excipient, the formulation adapted for use in a bath or soak. In some embodiments, the glucosamine or a pharmaceutically acceptable salt thereof is greater than 75% by weight of the composition. In some embodiments, the formulation further comprises chondroitin sulfate. In some embodiments, the formulation further comprises methylsulfonylmethane. In some embodiments, the pharmaceutically acceptable excipient is a transdermal permeation enhancer. In some embodiments, the pharmaceutically acceptable excipient is sea salt.

In another aspect, disclosed herein are methods of treating a subject suffering from osteoarthritis comprising administering to the subject glucosamine or a pharmaceutically acceptable salt thereof by immersion in a bath or soak. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the bath or soak has a concentration of glucosamine or a pharmaceutically acceptable salt thereof greater than 4 g/L. In further embodiments, the bath or soak has a concentration of glucosamine or a pharmaceutically acceptable salt thereof greater than 5 g/L. In still further embodiments, the bath or soak has a concentration of glucosamine or a pharmaceutically acceptable salt thereof greater than 6 g/L. In still further embodiments, the bath or soak has a concentration of glucosamine or a pharmaceutically acceptable salt thereof greater than 7 g/L. In some embodiments, the immersion involves at least 25% of the surface area of the subject. In further embodiments, the immersion involves at least 50% of the surface area of the subject. In still further embodiments, the immersion involves at least 75% of the surface area of the subject. In some embodiments, the immersion has a duration of greater than 15 minutes. In further embodiments, the immersion has a duration of greater than 30 minutes. In still further embodiments, the immersion has a duration of greater than 60 minutes. In some embodiments, the bath or soak has a temperature of about 34 to about 45 degrees Celsius. In further embodiments, the bath or soak has a temperature of about 34 to about 37 degrees Celsius. In other embodiments, the bath or soak has a temperature of about 38 to about 41 degrees Celsius. In other embodiments, the bath or soak has a temperature of about 42 to about 45 degrees Celsius. In some embodiments, administration is 1 to 5 times a day. In further embodiments, administration is 1 to 3 times a day. In still further embodiments, administration is once a day. In some embodiments, the treatment has a duration of greater than 1 week. In further embodiments, the treatment has a duration of greater than 4 weeks. In still further embodiments, the treatment has a duration of greater than 12 weeks. In some embodiments, the treatment has a duration of about 1 to about 12 weeks. In some embodiments, the method is effective to achieve a therapeutic blood plasma glucosamine level in a human subject. In some embodiments, the method is effective to achieve blood plasma glucosamine level of greater than 1 µg/ml in a human subject. In further embodiments, the method is effective to achieve blood plasma glucosamine level of greater than 2 µg/ml in a human subject. In some embodiments, the method further comprises administering to the subject chondroitin sulfate by immersion in the bath or soak. In some embodiments, the method further comprises administering to the subject methylsulfonylmethane by immersion in the bath or soak. In some embodiments, the method further comprises orally administering glucosamine or a pharmaceutically acceptable salt thereof to the subject. In further embodiments, the glucosamine or a pharmaceutically acceptable salt thereof is administered in a dose of about 100 mg to about 4,000 mg per day. In still further embodiments, the glucosamine or a pharmaceutically acceptable salt thereof is administered in a dose of about 500 mg to about 2,000 mg per day. In some embodiments, the method further comprises orally administering chondroitin sulphate to the subject. In further embodiments, the chondroitin sulphate is administered in a dose of about 100 mg to about 2,500 mg per day. In still further embodiments, the chondroitin sulphate is administered in a dose of about 400 mg to about 1,200 mg per day. In some embodiments, the method further comprises orally administering methylsulfonylmethane to the subject. In further embodiments, the methylsulfonylmethane is administered in a dose of about 100 mg to about 10,000 mg per day. In still further embodiments, the methylsulfonylmethane is administered in a dose of about 500 mg to about 7,000 mg per day.

In another aspect, disclosed herein are compositions for use in the treatment of osteoarthritis, the composition comprising glucosamine or a pharmaceutically acceptable salt thereof, the composition adapted for sublingual or buccal administration. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the composition further comprises chondroitin sulfate. In some embodiments, the composition further comprises methylsulfonylmethane.

In another aspect, disclosed herein are lozenges for use in the treatment of osteoarthritis, the lozenge comprising glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the lozenge further comprises chondroitin sulfate. In some embodiments, the lozenge further comprises methylsulfonylmethane.

In another aspect, disclosed herein are formulations for use in the treatment of osteoarthritis, the formulations comprising: glucosamine or a pharmaceutically acceptable salt thereof and a pharmaceutically acceptable excipient, the formulation adapted for sublingual or buccal administration. In some embodiments, the formulation further comprises chondroitin sulfate. In some embodiments, the formulation further comprises methylsulfonylmethane.

In another aspect, disclosed herein are methods of treating a subject suffering from osteoarthritis comprising sublingually or buccally administering to the subject glucosamine or a pharmaceutically acceptable salt thereof by a lozenge. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, administration is 1 to 5 times a day. In further embodiments, administration is 1 to 3 times a day. In still further embodiments, administration is once a day. In some embodiments, the treatment has a duration of greater than 1 week. In further embodiments, the treatment has a duration of greater than 4 weeks. In still further embodiments, the treatment has a duration of greater than 12 weeks. In some embodiments, the treatment has a duration of about 1 to about 12 weeks. In some embodiments, the method is effective to achieve a therapeutic blood plasma glucosamine level in a human subject. In some embodiments, the method is effective to achieve blood plasma glucosamine level of greater than 1 µg/ml in a human subject. In further embodiments, the method is effective to achieve blood plasma glucosamine level of greater than 2 µg/ml in a human subject. In some embodiments, the method further comprises administering to the subject chondroitin sulfate by the lozenge. In some embodiments, the method further comprises administering to the subject methylsulfonylmethane by the lozenge. In some embodiments, the method further comprises orally administering glucosamine to the subject. In further embodiments, the glucosamine is administered in a dose of about 100 mg to about 4,000 mg per day. In still further embodiments, the glucosamine is administered in a dose of about 500 mg to about 2,000 mg per day. In some embodiments, the method further comprises orally administering chondroitin sulphate to the subject. In further embodiments, the chondroitin sulphate is administered in a dose of about 100 mg to about 2,500 mg per day. In still further embodiments, the chondroitin sulphate is administered in a dose of about 400 mg to about 1,200 mg per day. In some embodiments, the method further comprises orally administering methylsulfonylmethane to the subject. In further embodiments, the methylsulfonylmethane is administered in a dose of about 100 mg to about 10,000 mg per day. In still further embodiments, the methylsulfonylmethane is administered in a dose of about 500 mg to about 7,000 mg per day.

In another aspect, disclosed herein are compositions for use in the treatment of osteoarthritis, the composition comprising glucosamine or a pharmaceutically acceptable salt thereof, the composition adapted for rectal administration. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the composition further comprises chondroitin sulfate. In some embodiments, the composition further comprises methylsulfonylmethane.

In another aspect, disclosed herein are suppositories for use in the treatment of osteoarthritis, the suppository comprising glucosamine or a pharmaceutically acceptable salt thereof. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the suppository further comprises chondroitin sulfate. In some embodiments, the suppository further comprises methylsulfonylmethane.

In another aspect, disclosed herein are formulations for use in the treatment of osteoarthritis, the formulation comprising: glucosamine or a pharmaceutically acceptable salt thereof and a pharmaceutically acceptable excipient, the formulation adapted for rectal administration. In some embodiments, the formulation further comprises chondroitin sulfate. In some embodiments, the formulation further comprises methylsulfonylmethane.

In another aspect, disclosed herein are methods of treating a subject suffering from osteoarthritis comprising rectally administering to the subject glucosamine or a pharmaceutically acceptable salt thereof by a suppository. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, administration is 1 to 5 times a day. In further embodiments, administration is 1 to 3 times a day. In still further embodiments, administration is once a day. In some embodiments, the treatment has a duration of greater than 1 week. In further embodiments, the treatment has a duration of greater than 4 weeks. In still further embodiments, the treatment has a duration of greater than 12 weeks. In some embodiments, the treatment has a duration of about 1 to about 12 weeks. In some embodiments, the method is effective to achieve a therapeutic blood plasma glucosamine level in a human subject. In some embodiments, the method is effective to achieve blood plasma glucosamine level of greater than 1 µg/ml in a human subject. In further embodiments, the method is effective to achieve blood plasma glucosamine level of greater than 2 µg/ml in a human subject. In some embodiments, the method further comprises administering to the subject chondroitin sulfate by the suppository. In some embodiments, the method further comprises administering to the subject methylsulfonylmethane by the suppository. In some embodiments, the method further comprises orally administering glucosamine to the subject. In further embodiments, the glucosamine is administered in a dose of about 100 mg to about 4,000 mg per day. In still further embodiments, the glucosamine is administered in a dose of about 500 mg to about 2,000 mg per day. In some embodiments, the method further comprises orally administering chondroitin sulphate to the subject. In further embodiments, the chondroitin sulphate is administered in a dose of about 100 mg to about 2,500 mg per day. In still further embodiments, the chondroitin sulphate is administered in a dose of about 400 mg to about 1,200 mg per day. In some embodiments, the method further comprises orally administering methylsulfonylmethane to the subject. In further embodiments, the methylsulfonylmethane is administered in a dose of about 100 mg to about 10,000 mg per day. In still further embodiments, the methylsulfonylmethane is administered in a dose of about 500 mg to about 7,000 mg per day.

In another aspect, disclosed herein are transdermal drug delivery patches comprising a backing layer, a drug-reservoir layer comprising pharmacologically active ingredients and a pharmaceutically acceptable excipient, and a release liner covering the drug-reservoir layer, the drug-reservoir layer comprising, as pharmacologically active ingredients, glucosamine or a pharmaceutically acceptable salt thereof, chondroitin sulfate, methylsulfonylmethane, the drug-reservoir layer further comprising, as a pharmaceutically acceptable excipient, a permeation enhancer. In some embodiments, the glucosamine or a pharmaceutically acceptable salt thereof is selected from the group consisting of: glucosamine, N-acetylglucosamine, glucosamine sulfate, glucosamine hydrochloride, and combinations thereof.

In another aspect, disclosed herein are topical creams comprising glucosamine or a pharmaceutically acceptable salt thereof, chondroitin sulfate, methylsulfonylmethane, and a pharmaceutically acceptable carrier. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the pharmaceutically acceptable carrier is propylene glycol. In some embodiments, the glucosamine or a pharmaceutically acceptable salt thereof comprises at least 25% by weight of the cream.

In another aspect, disclosed herein are methods of treating a subject having osteoarthritis, the method comprising: administering a to the subject a transdermal formulation comprising: glucosamine or a pharmaceutically acceptable salt thereof, chondroitin sulfate, methylsulfonylmethane, and a pharmaceutically acceptable excipient, wherein the transdermal formulation is in the form of: (a) topical formulation selected from the group consisting of: ointments, lotions, gels, pastes, aerosols, and creams, or (b) transdermal drug delivery patches. In some embodiments, the transdermal drug delivery patches are adhesive matrix patches. In some embodiments, the transdermal drug delivery patches are layered patches comprising a backing layer, a drug-reservoir layer, and a release liner covering the drug-reservoir layer. In some embodiments, the glucosamine or a pharmaceutically acceptable salt thereof is selected from the group consisting of: glucosamine, N-acetylglucosamine, glucosamine sulfate, glucosamine hydrochloride, and combinations thereof. In some embodiments, the method further comprises orally administering glucosamine or a pharmaceutically acceptable salt thereof to the subject. In further embodiments, the glucosamine or a pharmaceutically acceptable salt thereof is administered in a dose of about 100 mg to about 4,000 mg per day. In still further embodiments, the glucosamine or a pharmaceutically acceptable salt thereof is administered in a dose of about 500 mg to about 2,000 mg per day. In some embodiments, the method further comprises orally administering chondroitin sulphate to the subject. In further embodiments, the chondroitin sulphate is administered in a dose of about 100 mg to about 2,500 mg per day. In still further embodiments, the chondroitin sulphate is administered in a dose of about 400 mg to about 1,200 mg per day. In some embodiments, the method further comprises orally administering methylsulfonylmethane to the subject. In further embodiments, the methylsulfonylmethane is administered in a dose of about 100 mg to about 10,000 mg per day. In still further embodiments, the methylsulfonylmethane is administered in a dose of about 500 mg to about 7,000 mg per day.

DETAILED DESCRIPTION OF THE INVENTION

Figure 1:
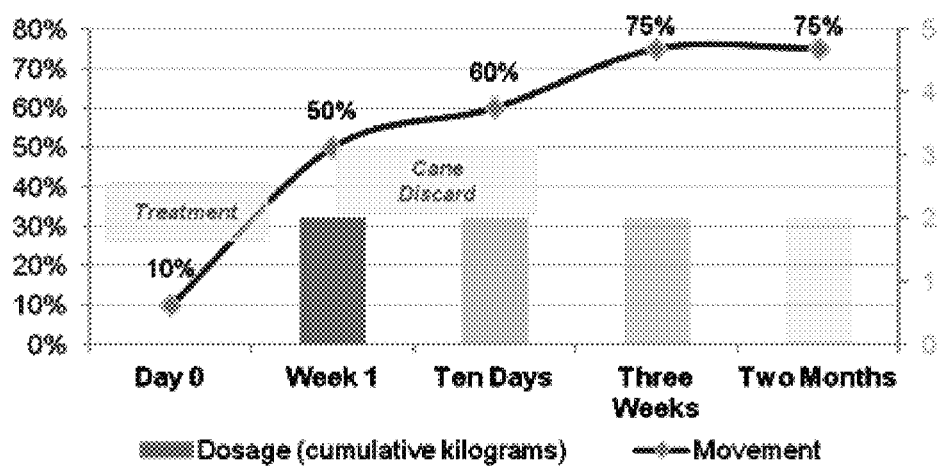
FIG. 1 shows the results of the treatment of a patient ("Mrs. Apple") with a glucosamine bath soak as described herein in Example 1.
Figure 2:
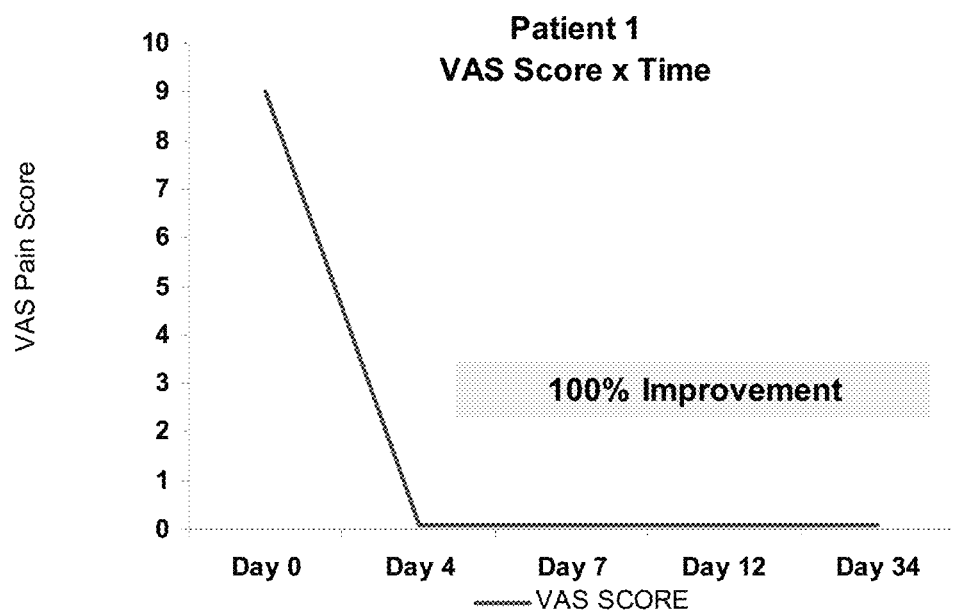
FIG. 2 shows the VAS score results of the treatment of Patient 1 with a glucosamine bath soak as described herein in Example 2.
Figure 3:
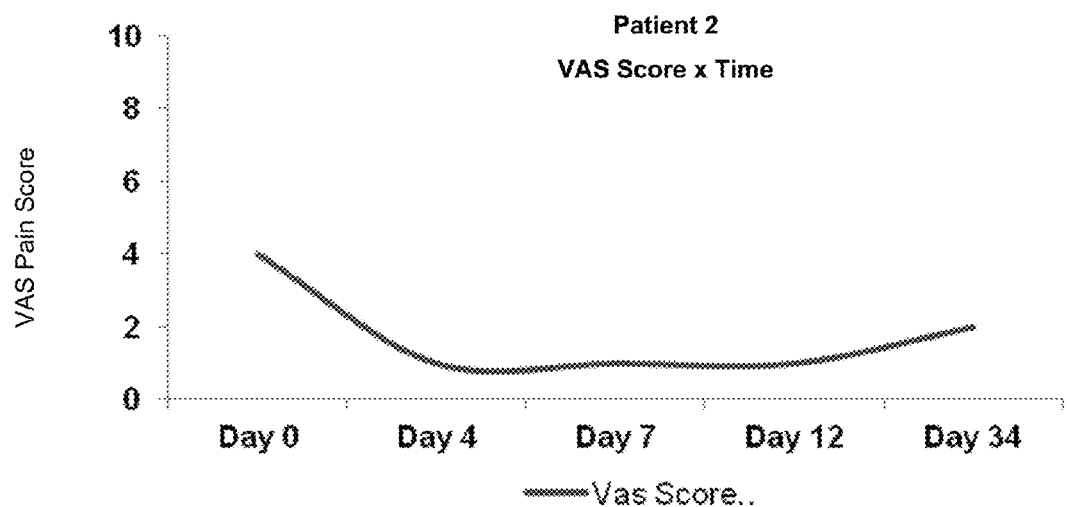
FIG. 3 shows the VAS score results of the treatment of Patient 2 with a glucosamine bath soak as described herein in Example 2.
Figure 4:
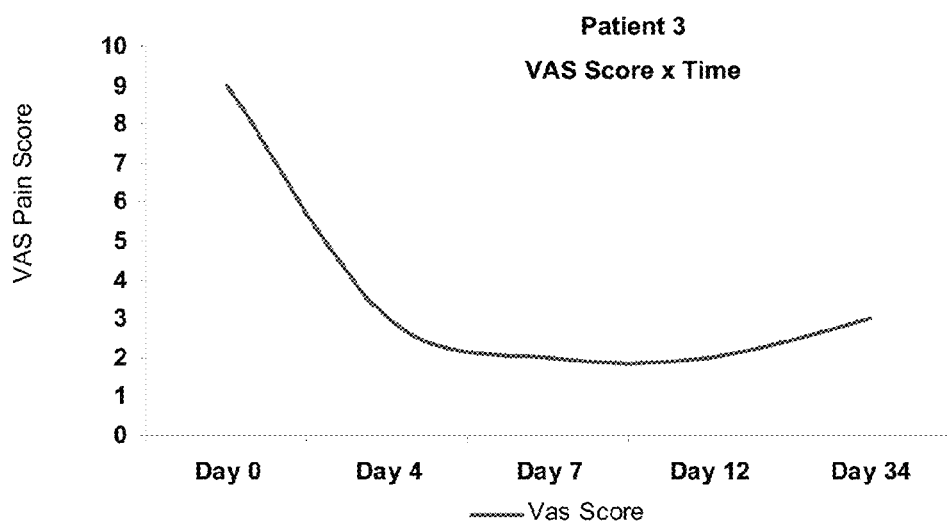
FIG. 4 shows the VAS score results of the treatment of Patient 3 with a glucosamine bath soak as described herein in Example 2.
Figure 5:
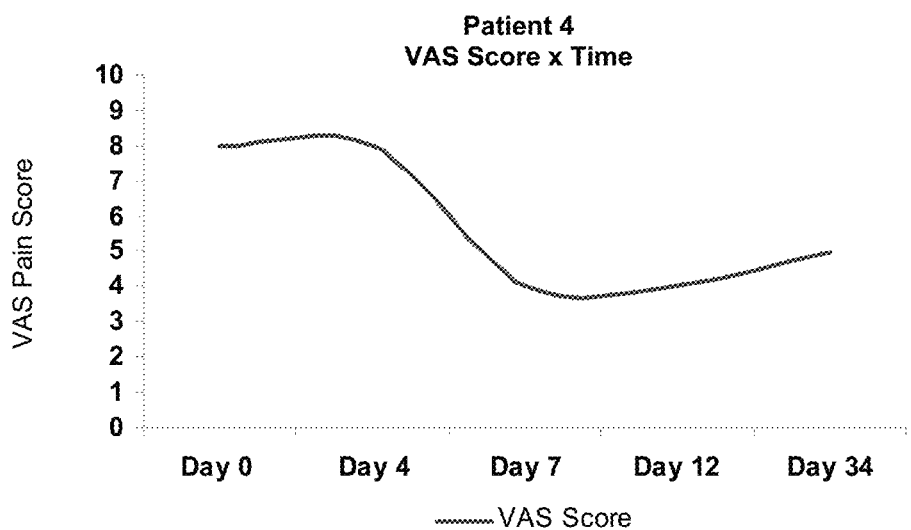
FIG. 5 shows the VAS score results of the treatment of Patient 4 with a glucosamine bath soak as described herein in Example 2.
Figure 6:
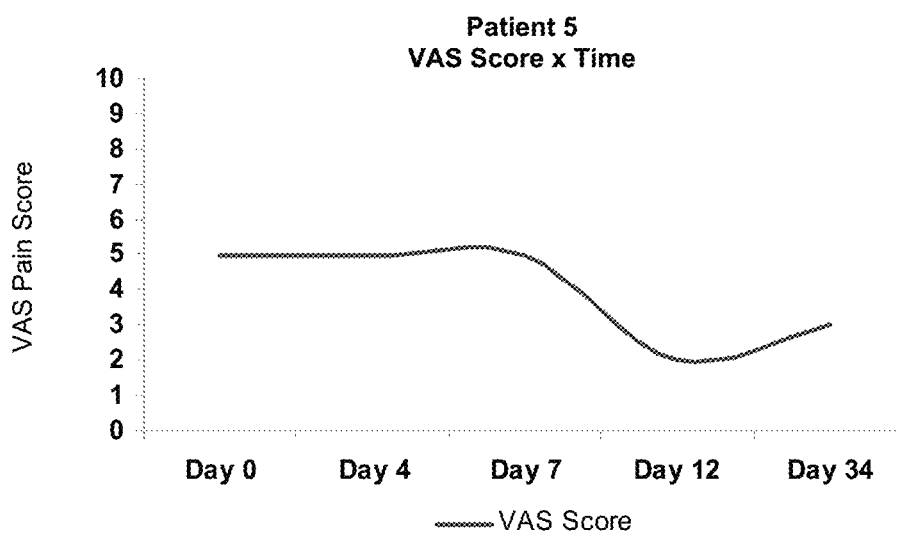
FIG. 6 shows the VAS score results of the treatment of Patient 5 with a glucosamine bath soak as described herein in Example 2.
Figure 7:
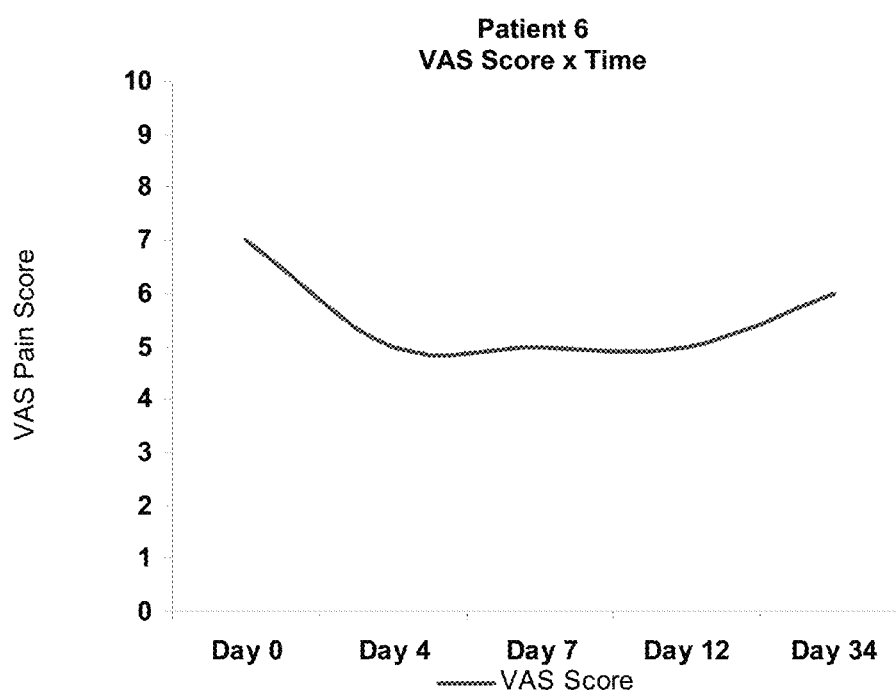
FIG. 7 shows the VAS score results of the treatment of Patient 6 with a glucosamine bath soak as described herein in Example 2.
Figure 8:
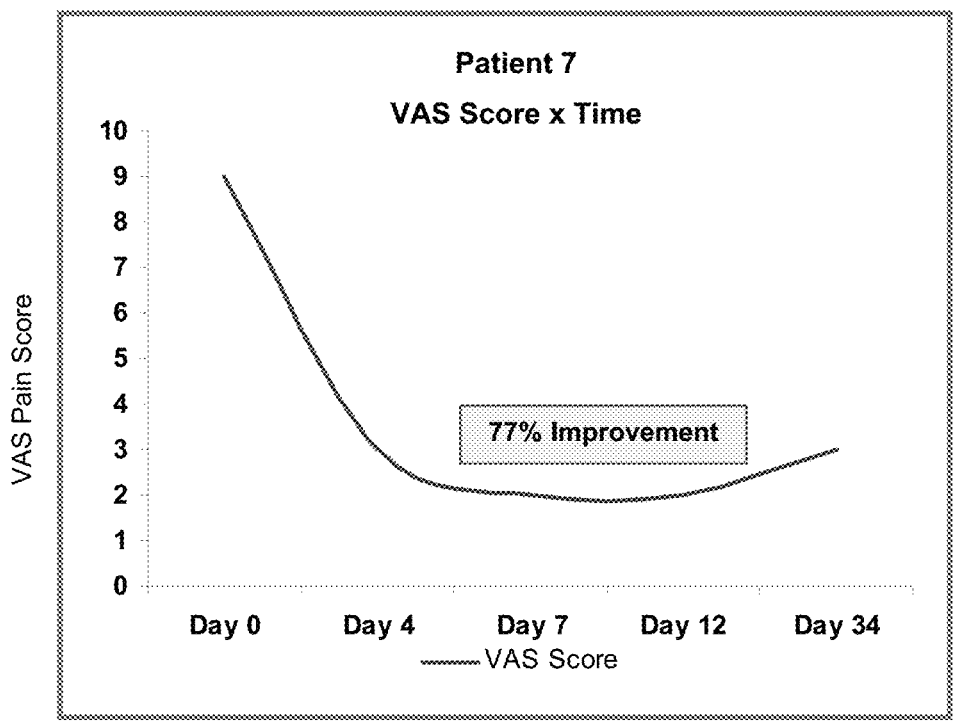
FIG. 8 shows the VAS score results of the treatment of Patient 7 with a glucosamine bath soak as described herein in Example 2.

Current and prior treatments for joint conditions such as osteoarthritis have failed to provide adequate bioavailability and in some cases have failed to clearly demonstrate efficacy. Moreover, osteoarthritis patients currently do not have adequate treatment options.

Described herein, in various embodiments, are compositions for use in the treatment of osteoarthritis, the composition comprising glucosamine or a pharmaceutically acceptable salt thereof, the composition adapted for use in a bath or soak.

Also described herein, in various embodiments, are bath beads for use in the treatment of osteoarthritis, the bath bead comprising glucosamine or a pharmaceutically acceptable salt thereof.

Also described herein, in various embodiments, are bath powders for use in the treatment of osteoarthritis, the bath powder comprising glucosamine or a pharmaceutically acceptable salt thereof.

Also described herein, in various embodiments, are bath salts for use in the treatment of osteoarthritis, the bath salt comprising glucosamine or a pharmaceutically acceptable salt thereof.

Also described herein, in various embodiments, are bath oils for use in the treatment of osteoarthritis, the bath oil comprising glucosamine or a pharmaceutically acceptable salt thereof.

Also described herein, in various embodiments, are kits for use in the treatment of osteoarthritis, the kit adapted for creating a bath or soak, the kit comprising about 500 g to about 3000 g of glucosamine or a pharmaceutically acceptable salt thereof.

Also described herein, in various embodiments, are methods of making a composition for use in the treatment of osteoarthritis, the composition adapted for use in a bath or soak, the method comprising the step of combining glucosamine or a pharmaceutically acceptable salt thereof and a transdermal permeation enhancer.

Also described herein, in various embodiments, are formulations for use in the treatment of osteoarthritis, the formulation comprising: glucosamine or a pharmaceutically acceptable salt thereof and a pharmaceutically acceptable excipient, the formulation adapted for use in a bath or soak.

Also described herein, in various embodiments, are methods of treating a subject suffering from osteoarthritis comprising administering to the subject glucosamine or a pharmaceutically acceptable salt thereof by immersion in a bath or soak.

Also described herein, in various embodiments, are compositions for use in the treatment of osteoarthritis, the composition comprising glucosamine or a pharmaceutically acceptable salt thereof, the composition adapted for sublingual or buccal administration.

Also described herein, in various embodiments, are lozenges for use in the treatment of osteoarthritis, the lozenge comprising glucosamine or a pharmaceutically acceptable salt thereof.

Also described herein, in various embodiments, are formulations for use in the treatment of osteoarthritis, the formulations comprising: glucosamine or a pharmaceutically acceptable salt thereof and a pharmaceutically acceptable excipient, the formulation adapted for sublingual or buccal administration.

Also described herein, in various embodiments, are methods of treating a subject suffering from osteoarthritis comprising sublingually or buccally administering to the subject glucosamine or a pharmaceutically acceptable salt thereof by a lozenge.

Also described herein, in various embodiments, are compositions for use in the treatment of osteoarthritis, the composition comprising glucosamine or a pharmaceutically acceptable salt thereof, the composition adapted for rectal administration.

Also described herein, in various embodiments, are suppositories for use in the treatment of osteoarthritis, the suppository comprising glucosamine or a pharmaceutically acceptable salt thereof.

Also described herein, in various embodiments, are formulations for use in the treatment of osteoarthritis, the formulation comprising: glucosamine or a pharmaceutically acceptable salt thereof and a pharmaceutically acceptable excipient, the formulation adapted for rectal administration.

Also described herein, in various embodiments, are methods of treating a subject suffering from osteoarthritis comprising rectally administering to the subject glucosamine or a pharmaceutically acceptable salt thereof by a suppository.

Also described herein, in various embodiments, are transdermal drug delivery patches comprising a backing layer, a drug-reservoir layer comprising pharmacologically active ingredients and a pharmaceutically acceptable excipient, and a release liner covering the drug-reservoir layer, the drug-reservoir layer comprising, as pharmacologically active ingredients, glucosamine or a pharmaceutically acceptable salt thereof, chondroitin sulfate, methylsulfonylmethane, the drug-reservoir layer further comprising, as a pharmaceutically acceptable excipient, a permeation enhancer.

Also described herein, in various embodiments, are topical creams comprising glucosamine or a pharmaceutically acceptable salt thereof, chondroitin sulfate, methylsulfonylmethane, and a pharmaceutically acceptable carrier.

Also described herein, in various embodiments, are methods of treating a subject having osteoarthritis, the method comprising: administering a to the subject a transdermal formulation comprising: glucosamine or a pharmaceutically acceptable salt thereof, chondroitin sulfate, methylsulfonylmethane, and a pharmaceutically acceptable excipient, wherein the transdermal formulation is in the form of: (a) topical formulation selected from the group consisting of: ointments, lotions, gels, pastes, aerosols, and creams, or (b) transdermal drug delivery patches.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, the "transdermal and transmucosal glucosamine products" refers to any composition, article of manufacture, or kit described herein comprising glucosamine or a pharmaceutically acceptable salt thereof and adapted for provision of glucosamine or a pharmaceutically acceptable salt thereof via one or more transdermal or transmucosal routes. In some embodiments, the transdermal and transmucosal glucosamine products include, but are not limited to baths, soaks, bath beads, bath powders, bath salts, and bath oils. In some embodiments, the transdermal and transmucosal glucosamine products include, but are not limited to lozenges, suppositories, transdermal patches, and topical creams, gels, ointments, and the like.

Conditions

The transdermal and transmucosal glucosamine products, compositions adapted therefor, and methods of treatment using the same, described herein are suitable for the treatment of a wide range of conditions. In some embodiments, the products, compositions, and methods described herein are suitable for the treatment of pain. In some embodiments, the products, compositions, and methods described herein are suitable for the treatment of inflammation. In some embodiments, the products, compositions, and methods described herein are suitable for the treatment of injury. In some embodiments, the products, compositions, and methods described herein are suitable for the treatment of a condition involving, by way of non-limiting examples, muscle pain, muscle injury, muscle strain, tendon injury, tendon strain, tendon inflammation, ligament injury, ligament strain, ligament inflammation, joint degradation, joint injury, joint wear and tear, joint inflammation, and/or joint pain.

In some embodiments, the products, compositions, and methods described herein are suitable for the treatment of pain. In further embodiments, the products, compositions, and methods described herein are suitable for the treatment of pain associated with one or more conditions described herein. For example in various embodiments, the products, compositions, and methods described herein are suitable for the treatment of joint pain, muscle pain, tendon pain, ligament pain, neck pain, lower back pain, hip pain, knee pain, ankle pain, foot pain, toe pain, shoulder pain, elbow pain, hand pain, and/or finger pain.

In further embodiments, neck pain is associated with one or more of cervical facet joint (zygapophyseal joint) disease/pain/arthritis, cervical discogenic pain, cervical radiculopathy, brachial plexopathy, neck ligament strain, and/or neck muscle strain. In further embodiments, lower back pain is associated with one or more of lumbar facet joint (zygapophyseal joint) disease/pain/arthritis, lumbar discogenic pain, sacroiliac joint pain, sciatica, lumbosacral radiculopathy, back ligament strain, and/or back muscle strain. In further embodiments, hip pain is associated with one or more of hip bursitis, iliotibial band pain, hip labral tear, hip impingement syndrome, and/or iliopsoas tendonitis. In further embodiments, knee pain is associated with one or more of knee meniscus tear, knee ligament strain, knee tendonitis, patellofemoral syndrome (chondromalacia patella), and/or osteochondritis dissecans. In further embodiments, ankle pain is associated with one or more of ankle sprain and/or osteochondritis dissecans. In further embodiments, foot pain is associated with one or more of metatarsal arthritis, metatarsalgia, plantar fasciitis, and/or calcaneus spur. In further embodiments, shoulder pain is associated with one or more of, shoulder impingement syndrome, rotator cuff tear, shoulder labrum tear, biceps tendonitis, and/or rotator cuff tendonitis. In further embodiments, elbow pain is associated with one or more of lateral epicondylitis, medial epicondylitis, and/or olecranon bursitis. In further embodiments, hand pain is associated with carpal tunnel syndrome.

In some embodiments, the products, compositions, and methods described herein are suitable for the treatment of inflammation. In further embodiments, the products, compositions, and methods described herein are suitable for the treatment of inflammation associated with one or more conditions described herein. For example, in various embodiments, the products, compositions, and methods described herein are suitable for the treatment of joint inflammation, muscle inflammation, tendon inflammation, ligament inflammation, neck inflammation, lower back inflammation, hip inflammation, knee inflammation, ankle inflammation, foot inflammation, toe inflammation, shoulder inflammation, elbow inflammation, hand inflammation, and/or finger inflammation.

In some embodiments, the products, compositions, and methods described herein are suitable for the treatment of arthritis. In further embodiments, the arthritis is psoriatic arthritis, juvenile idiopathic arthritis, septic arthritis, rheumatoid arthritis, or osteoarthritis. In various embodiments, the arthritis affects one or more of the neck, lower back, hip, knee, ankle, foot, toe, shoulder, elbow, hand, and/or finger. In a specific embodiment, the products, compositions, and methods described herein are suitable for the treatment of osteoarthritis of for example, the neck, lower back, hip, knee, ankle, foot, toe, shoulder, elbow, hand, and/or finger.

In some embodiments, the products, compositions, and methods described herein are suitable for the treatment of injury to, by way of non-limiting examples, joints, muscles, tendons, and ligaments. In further embodiments, a joint injury is a knee meniscus tear. In some embodiments, the products, compositions, and methods described herein are suitable for the prevention of joint, muscle, tension, and ligament injury.

In some embodiments, the products, compositions, and methods described herein are suitable for the treatment of other conditions including, by way of non-limiting examples, fibromyalgia, lupus, tendonitis, bursitis, gout, pseudo-gout, cervical radiculopathy, lumbar radiculopathy, spondyloarthropathies, ankylosing spondylitis, chronic fatigue syndrome, complex regional pain syndrome, and/or cervicogenic headache.

Glucosamine

In some embodiments, the transdermal and transmucosal glucosamine products, compositions adapted therefor, and methods of treatment using the same, described herein include glucosamine or a pharmaceutically acceptable salt thereof. Glucosamine is available in several suitable chemical forms. In further embodiments, the glucosamine or a pharmaceutically acceptable salt thereof is glucosamine and/or N-acetylglucosamine. Many salts of glucosamine are suitable. In some embodiments, the glucosamine or a pharmaceutically acceptable salt thereof is glucosamine sulfate, glucosamine hydrochloride, or both. In still further embodiments, the glucosamine or a pharmaceutically acceptable salt thereof is a combination of two or more of the forms described herein.

Glucosamine (molecular formula $C_6H_{13}NO_5$) is a naturally occurring monosaccharide amino sugar. Glucosamine is also known as (3R,4R,5S)-3-Amino-6-(hydroxymethyl)oxane-2,4,5-triol and 2-Amino-2-deoxy-glucose Chitosamine. Glucosamine is commercially available as an oral, non-vitamin, non-mineral, dietary supplement.

In some embodiments, the transdermal and transmucosal glucosamine products, compositions adapted therefor, and methods of treatment using the same, described herein include glucosamine or a pharmaceutically acceptable salt thereof in combination with one or more additional medications or supplements. By way of non-limiting examples, in some embodiments, glucosamine or a pharmaceutically acceptable salt thereof is combined with chondroitin (e.g., chondroitin sulfate), methylsulfonylmethane, hyaluronic acid, omega 3 fatty acids (e.g., eicosapentaenoic acid, docosahexaenoic acid, α-linolenic acid, etc.), vitamin D, vitamin C, quercetin, avocado soybean unsaponifiables (ASU), anti-oxidant berry extracts (e.g., blueberries, agai berry, maqui berry, chokeberry, etc.), COX inhibitors (e.g., non-steroidal anti-inflammatory drugs), turmeric (*Curcuma longa*), bromelain, and combinations thereof.

In some embodiments, the transdermal and transmucosal glucosamine products, compositions adapted therefor, and methods of treatment using the same, described herein include glucosamine or a pharmaceutically acceptable salt thereof and chondroitin. Chondroitin sulfate is a sulfated glycosaminoglycan (GAG) composed of an unbranched polysaccharide chain of variable length containing two alternating monosaccharides: D-glucuronic acid (GlcA) and N-acetyl-D-galactosamine (GalNAc). In some cases, a chondroitin chain is composed of over 100 individual sugars, each of which can be sulfated in variable positions and quantities. Chondroitin sulfate is an important structural component of cartilage and provides much of its resistance to compression. Chondroitin sulfate is commercially available as a dietary supplement.

In some embodiments, the transdermal and transmucosal glucosamine products, compositions adapted therefor, and methods of treatment using the same, described herein include glucosamine or a pharmaceutically acceptable salt thereof and methylsulfonylmethane. Methylsulfonylmethane (molecular formula $C_2H_6O_2S$; structural formula $(CH_3)_2SO_2$) is an organosulfur compound. It is also known by several other names including MSM, $DMSO_2$, methyl sulfone, and dimethyl sulfone. Methylsulfonylmethane is commercially available as a dietary supplement.

In further embodiments, the transdermal and transmucosal glucosamine products, compositions adapted therefor, and methods of treatment using the same, described herein include glucosamine or a pharmaceutically acceptable salt thereof, chondroitin, and methylsulfonylmethane.

In some embodiments, the transdermal and transmucosal glucosamine products, compositions adapted therefor, and methods of treatment using the same, described herein include glucosamine or a pharmaceutically acceptable salt thereof and hyaluronic acid. Hyaluronic acid is an anionic, nonsulfated glycosaminoglycan (GAG), also known as hyaluronan. Hyaluronic acid is a polymer of disaccharides, themselves composed of D-glucuronic acid and N-acetyl-D-glucosamine, linked via alternating β-1,4 and β-1,3 glycosidic bonds.

Bath or Soak

In some embodiments, described herein are baths and soaks comprising glucosamine or a pharmaceutically acceptable salt thereof, compositions and formulations adapted therefor, and methods of treatment using the same. In further embodiments, described herein are bath beads, bath powders, bath salts, bath oils, and kits comprising glucosamine or a pharmaceutically acceptable salt thereof, compositions adapted therefor, and methods of treatment using the same.

In some embodiments, the baths and soaks, including bath products, compositions, and methods are suitable for immersion therapy. In further embodiments, immersion therapy involves partially or completely immersing a subject's body in a medication or supplement in order to raise the blood plasma level of that medication or supplement. In some cases, advantages of immersion therapy include, but are not limited to, introducing a medication or supplement into the blood without risking breakdown in the gastrointestinal system, without risking direct irritation of the gastrointestinal system, and without requiring inhalation or injections.

In some embodiments, the intent of immersion therapy is to maximize systemic absorption in order to increase blood plasma concentration of the medication or supplement. There are several variables involved with immersion therapy that a skilled artisan should consider. These variable are illustrated in the following formula:

$$Ba=(Ab)(A)(T) \qquad \text{Formula 1}$$

Where Ba=blood absorption of the supplement or medication;

Ab=the absorption constant of the supplement or medication through the skin;

A=surface area of skin exposed to the supplement or medication; and

T=time exposed to the medication or supplement.

A of Formula 1 has many suitable values. In various embodiments, suitable percentages of a subject's skin immersed in the bath or soak are about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or more percent, including increments therein. In various embodiments, the surface area of skin exposed to the supplement or medication is greater than 1, 2, 3, 4, 5, 10, 15, 20, 25, 30, 35, 40, 45, 50, 55, 60, 65, 70, 75, 80, 85, 90, 95, 96, 97, 98, and 99 percent, including increments therein. In other various embodiments, the surface area of skin exposed to the supplement or medication is less than 99, 98, 97, 96, 95, 90, 85, 80, 75, 70, 65, 60, 55, 50, 45, 40, 35, 30, 25, 20, 15, 10, 9, 8, 7, 6, 5, 4, 3, 2, and 1 percent, including increments therein. In some embodiments, the surface area of skin exposed to the supplement or medication is between 100 and 5 percent, between 90 and 15 percent, between 80 and 25 percent, or between 70 and 35 percent. In a particular embodiment, the surface area of skin exposed to the supplement or medication is greater than ⅙ of the body surface area.

T of Formula 1 has many suitable values. In various embodiments, suitable durations for the bath or soak are about 1, 2, 3, 4, 5, 6, 7, 8, 9, 10, 15, 20, 25, 30, 35, 40, 45, 50, 55, and 60 minutes, including increments therein. In further various embodiments, suitable durations for the bath or soak are about 1, 2, 3, 4, 5, 6, 7, 8, 9, and 10 hours, including increments therein. In various embodiments, the time the subject is exposed to the medication or supplement is greater than 1, 2, 3, 4, 5, 10, 15, 20, 25, 30, 35, 40, 45, 50, 55, and 60 minutes, including increments therein. In further various embodiments, the time the subject is exposed to the medication or supplement is greater than 1, 2, 3, 4, 5, 6, 7, 8, 9, and 10 hours, including increments therein. In other various embodiments, the time the subject is exposed to the medication or supplement is less than 20, 19, 18, 17, 16, 15, 14, 13, 12, 11, 10, 9, 8, 7, 6, 5, 4, 3, 2, and 1 hour, including increments therein. In further various embodiments, the time the subject is exposed to the medication or supplement is less than 60, 55, 50, 45, 40, 35, 30, 25, 20, 15, 10, and 5 minutes, including increments therein. In some embodiments, the time the subject is exposed to the medication or supplement is between 30 seconds and 10 hours, between 45 seconds and 8 hours, or between 1 minute and 6 hours. In a particular embodiment, the time the subject is exposed to the medication or supplement is greater than 1 minute and less than 5 hours.

Many temperatures for the water in which the subject is immersed are suitable. In various embodiments, suitable temperatures include about 30, 31, 32, 33, 34, 35, 36, 37, 38, 39, 40, 41, 42, 43, 44, 45, 46, 47, and 48 degrees Celsius, including increments therein. In some embodiments, the temperature of the water in which the subject is immersed is greater than 30, 31, 32, 33, 34, 35, 36, 37, 38, 39, 40, 41, 42, 43, 44, 45, 46, and 47 degrees Celsius. In some embodiments, the temperature of the water in which the subject is immersed is less than 47, 46, 45, 44, 43, 42, 41, 40, 39, 38, 37, 36, 35, 34, 33, 32, 31, and 30 degrees Celsius. In some embodiments, the bath or soak is cold and has a temperature of from 34 to 37 degrees Celsius. In other embodiments, the bath or soak is warm and has a temperature of from 38 to 41 degrees Celsius. In some embodiments, the bath or soak is hot and has a temperature of from 42 to 45 degrees Celsius.

In some embodiments, the temperature of the water in which the subject is immersed is greater than about 37 degrees Celsius as this increases capillary dilation and will increase potential absorption of the medication or supplement. When absorption rates at different temperatures are known, then Ab of Formula 1 in the immersion therapy equation will reflect the absorption rate at that particular temperature. In some embodiments, the subject takes a shower or otherwise rinses the skin before entering a bath or soak in order to eradicate excess skin oil which would otherwise interfere with absorption. In other embodiments, this is not a required step of immersion therapy.

In a particular embodiment, immersion therapy involves partially or completely immersing a subject's body in a glucosamine solution (e.g., a bath or soak) in order to raise the blood plasma level of glucosamine. In a further embodiment, immersion therapy with a glucosamine solution elevates blood plasma levels of glucosamine to support optimal joint function.

A wide range of amounts of glucosamine are suitably added to liquid to create a bath or soak with a wide range of suitable glucosamine concentrations. In various embodiments, suitable quantities of glucosamine for the bath or soak are about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and 5000 grams, including increments therein. In other various embodiments, suitable quantities of glucosamine for the bath or soak are greater than 100, 500, 1000, 1500, 2000, 2500, 3000, 3500, and 4000 grams, including increments therein. In yet other various embodiments, suitable quantities of glucosamine for the bath or soak are less than 4000, 3500, 3000, 2500, 2000, 1500, 1000, 500, and 100 grams, including increments therein. In some embodiments, the quantity of glucosamine added to the bath or soak is between 500 and 750 grams, between 750 and 1000 grams, between 1000 and 1250 grams, between 1250 and 1500 grams, between 1500 and 1750 grams, between 1750 and 2000 grams, between 2000 and 2250 grams, between 2250 and 2500 grams, between 2500 and 2750 grams, between 2750 and 3000 grams, between 3000 and 3250 grams, between 3250 and 3500 grams, between 3500 and 3750 grams, or between 3750 and 4000 grams.

In some embodiments, the quantity of glucosamine is determined based on the BMI of the subject. For example, a subject with a high BMI is optionally exposed to a higher overall quantity of glucosamine and/or a higher concentration of glucosamine in a bath or soak. Conversely, a subject with a low BMI is optionally exposed to a lower overall quantity of glucosamine and/or a lower concentration of glucosamine in a bath or soak. In other embodiments, the quantity of glucosamine is determined based on the severity of the condition or symptoms of the subject.

Exemplary glucosamine bath/soak parameters are provided in Tables 1-3 below:

TABLE 1

Cool Bath

| Body Mass Index (BMI)* | Glucosamine Quantity (g) | Temperature (degrees C.) | Tub Size (liters)** | Soak Duration (mins) |
| --- | --- | --- | --- | --- |
| <18.5 | 1000-1500 | 34-37 | 150 | 60 |
| 18.5-24.9 | 1500-2000 | 34-37 | 150 | 60 |

TABLE 1-continued

Cool Bath

| Body Mass Index (BMI)* | Glucosamine Quantity (g) | Temperature (degrees C.) | Tub Size (liters)** | Soak Duration (mins) |
| --- | --- | --- | --- | --- |
| 25.0-29.9 | 2000-2500 | 34-37 | 150 | 60 |
| >30.0 | 2500-3000 | 34-37 | 150 | 60 |

*Uses CDC BMI categories for underweight, normal, overweight, and obese individuals (available at: www.cdc.gov/healthyweight/assessing/bmi/adult_bmi/index.html).
**Estimate assumes a 60 gallon (227 L) tub ⅔ full. This is a slightly larger tub. Older tubs may be significantly smaller (e.g., 40 gallon).

TABLE 2

Warm Bath

| Body Mass Index (BMI) | Glucosamine Quantity (g) | Temperature (degrees C.) | Tub Size (liters) | Soak Duration (mins) |
| --- | --- | --- | --- | --- |
| <18.5 | 750-1000 | 38-41 | 150 | 60 |
| 18.5-24.9 | 1000-1250 | 38-41 | 150 | 60 |
| 25.0-29.9 | 1250-1500 | 38-41 | 150 | 60 |
| >30.0 | 1500-1750 | 38-41 | 150 | 60 |

TABLE 3

Hot Bath

| Body Mass Index (BMI) | Glucosamine Quantity (g) | Temperature (degrees C.) | Tub Size (liters) | Soak Duration (mins) |
| --- | --- | --- | --- | --- |
| <18.5 | 500-750 | 42-45 | 150 | 60 |
| 18.5-24.9 | 750-1000 | 42-45 | 150 | 60 |
| 25.0-29.9 | 1000-1250 | 42-45 | 150 | 60 |
| >30.0 | 1250-1500 | 42-45 | 150 | 60 |

A bath or soak described herein is optionally prepared in a wide range of suitable volumes of liquid (e.g., water). In some embodiments, a bath or soak described herein is prepared in a typical bathing tub found, for example, in a home, a hospital, a physical rehabilitation facility, or a gym. In various embodiments, suitable volumes of liquid for the bath or soak are about 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, and 300 liters, including increments therein. In other various embodiments, suitable volumes of liquid for the bath or soak are greater than 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, and 300 liters, including increments therein. In yet other various embodiments, suitable volumes of liquid for the bath or soak are less than 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, and 300 liters, including increments therein. In some embodiments, the bath or soak has a volume of liquid between 10 and 50 liters, between 50 and 100 liters, between 100 and 150 liters, between 150 and 200 liters, between 200 and 250 liters, or between 250 and 300 liters.

The quantities of glucosamine described herein and the volumes of liquid described herein are optionally combined to create a bath or soak with a wide range of suitable glucosamine concentrations. In various embodiments, suitable glucosamine concentrations for the bath or soak are about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, and 14.0 grams per liter, including increments therein. In other various embodiments, suitable glucosamine concentrations for the bath or soak are about 15, 20, 25, 30, 35, 40, 45, 50, 55, 60, 65, 70, 75, 80, 85, and 90 grams per liter, including increments therein. In some embodiments, suitable glucosamine concentrations for the bath or soak are greater than 1, 2, 3, 4, 5, 6, 7, 8, 9, 10, 11, 12, 13, 14, 15, 20, 25, 30, 35, 40, 45, 50, 55, 60, 65, 70, 75, 80, 85, and 90 grams per liter, including increments therein. In other embodiments, suitable glucosamine concentrations for the bath or soak are less than 90, 85, 80, 75, 70, 65, 60, 55, 50, 45, 40, 35, 30, 25, 20, 15, 14, 13, 12, 11, 10, 9, 8, 7, 6, 5, 4, 3, 2, and 1 gram per liter, including increments therein. In a particular embodiment, the bath or soak has a concentration of about 7 grams of glucosamine per liter of liquid (e.g., water).

Compositions and Formulations for Bath or Soak

Disclosed herein, in some embodiments, are compositions and formulations comprising glucosamine or a pharmaceutically acceptable salt thereof adapted for use in a bath or soak. In further embodiments, the glucosamine or a pharmaceutically acceptable salt thereof is selected from glucosamine, N-acetylglucosamine, glucosamine sulfate, glucosamine hydrochloride, and combinations thereof.

A composition or formulation adapted for use in a bath or soak suitably has a wide range of amounts of glucosamine. In various embodiments, the compositions and formulations adapted for use in a bath or soak described herein comprise about 1%, 5%, 10%, 15%, 20%, 25%, 30%, 35%, 40%, 45%, 50%, 55%, 60%, 65%, 70%, 75%, 80%, 85%, or 90% w/w glucosamine, including increments therein. In some embodiments, the compositions and formulations adapted for use in a bath or soak described herein comprise greater than 1%, 5%, 10%, 20%, 30%, 40%, 50%, 60%, 70%, 80%, or 90% w/w glucosamine, including increments therein. In further embodiments, the compositions and formulations adapted for use in a bath or soak described herein comprise about 1% to about 10% w/w glucosamine, about 10% to about 20% w/w glucosamine, about 20% to about 30% w/w glucosamine, about 30% to about 40% w/w glucosamine, about 40% to about 50% w/w glucosamine, about 50% to about 60% w/w glucosamine, about 60% to about 70% w/w glucosamine, or about 70% to about 80% w/w glucosamine.

In some embodiments, the compositions comprising glucosamine or a pharmaceutically acceptable salt thereof adapted for use in a bath or soak further comprise an additional medication or supplement. In further embodiments, the compositions comprise chondroitin or a pharmaceutically acceptable salt thereof, methylsulfonylmethane, or both.

A wide range of amounts of chondroitin are suitably added to liquid in addition to glucosamine to create a bath or soak with a wide range of suitable glucosamine and chondroitin concentrations. In various embodiments, suitable quantities of chondroitin for the bath or soak are about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and 5000 grams or more, including increments therein. In a particular embodiment, the compositions comprising glucosamine or a pharmaceutically acceptable salt thereof adapted for use in a bath or soak further comprise about 200 to about 3000 grams of chondroitin. In various embodiments, the compositions and formulations adapted for use in a bath or soak described herein comprise about 1%, 5%, 10%, 15%, 20%, 25%, 30%, 35%, 40%, 45%, 50%, 55%, 60%, 65%, 70%, 75%, 80%, 85%, or 90% w/w chondroitin, including increments therein. In some embodiments, the compositions and formulations adapted for use in a bath or soak described herein comprise greater than 1%, 5%, 10%, 20%, 30%, 40%, 50%, 60%, 70%, 80%, or 90% w/w chondroitin, including increments therein. In further embodiments, the compositions and formulations adapted for use in a bath or soak described herein comprise about 1% to about 10% w/w chondroitin, about 10% to about 20% w/w chondroitin, about 20% to about 30% w/w chondroitin, about 30% to about 40% w/w chondroitin, about 40% to about 50% w/w chondroitin, about 50% to about 60% w/w chondroitin, or about 60% to about 70% w/w chondroitin.

A wide range of amounts of methylsulfonylmethane are suitably added to liquid in addition to glucosamine to create a bath or soak with a wide range of suitable glucosamine and methylsulfonylmethane concentrations. In various embodiments, suitable quantities of methylsulfonylmethane for the bath or soak are about 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, and 7000 grams or more, including increments therein. In a particular embodiment, the compositions comprising glucosamine or a pharmaceutically acceptable salt thereof adapted for use in a bath or soak further comprise about 500 to about 5000 grams of methylsulfonylmethane. In various embodiments, the compositions and formulations adapted for use in a bath or soak described herein comprise about 1%, 5%, 10%, 15%, 20%, 25%, 30%, 35%, 40%, 45%, 50%, 55%, 60%, 65%, 70%, or 75% w/w methylsulfonylmethane, including increments therein. In some embodiments, the compositions and formulations adapted for use in a bath or soak described herein comprise greater than 1%, 5%, 10%, 20%, 30%, 40%, 50%, 60%, or 70% w/w methylsulfonylmethane, including increments therein. In further embodiments, the compositions and formulations adapted for use in a bath or soak described herein comprise about 1% to about 10% w/w methylsulfonylmethane, about 10% to about 20% w/w methylsulfonylmethane, about 20% to about 30% w/w methylsulfonylmethane, about 30% to about 40% w/w methylsulfonylmethane, about 40% to about 50% w/w methylsulfonylmethane, or about 60% to about 70% w/w methylsulfonylmethane.

TABLE 4

Exemplary Bath or Soak Compositions

| Body Mass Index (BMI) | Glucosamine (g) | Chondroitin (g) | Methylsulfonylmethane (g) | Permeation Enhancer |
|---|---|---|---|---|
| <18.5 | 500-750 | optionally 200-900 | optionally 500-1625 | Sea Salts |
| 18.5-24.9 | 750-1000 | optionally 900-1600 | optionally 1625-2750 | Sea Salts |
| 25.0-29.9 | 1000-1250 | optionally 1600-2300 | optionally 2750-3875 | Sea Salts |
| >30.0 | 1250-1500 | optionally 2300-3000 | optionally 3875-5000 | Sea Salts |

In some cases, the stratum corneum, the outermost layer of the epidermis, consisting of dead cells (corneocytes), presents a significant barrier to topical administration of a medication or supplement. Accordingly, in some embodiments, the compositions comprising glucosamine or a pharmaceutically acceptable salt thereof adapted for use in a bath or soak further comprise a transdermal permeation enhancer. In further embodiments, the transdermal permeation enhancer promotes transdermal penetration of the glucosamine. In some embodiments, the transdermal permeation enhancer comprises one or more of: sea salt, urea, a sulphoxide, an azone, an oxazolidinone, a pyrrolidone, a fatty alcohol, a fatty acid ester, a fatty acid, a fatty alcohol ether, an enzyme, a surfactant, an essential oil, a terpene, and a terpenoid. In further embodiments, where a transdermal permeation enhancer comprises sea salts or dead sea salts, the salt includes one or more of: sodium chloride, magnesium chloride, potassium chloride, and magnesium sulfate. In some embodiments, sea salts and/or dead sea salts used in immersion therapy (e.g., in a bath, soak, etc.) create an osmotic gradient to facilitate, accelerate, and/or enhance absorption of one or more medications or supplements.

In some embodiments, during immersion therapy, a subject is encouraged to use any other bath gel, salt, scent, or other agent in order to make, for example, a bath or soak a more enjoyable experience. In further embodiments, an important goal in immersion therapy is the introduction of a medication or supplement during the immersion of the body in water. To this goal, in some cases, the medication or supplement is used in combination with any number of other ingredients (e.g., excipients, etc.). Accordingly, in various embodiments, compositions and formulations adapted for use in a bath or soak described herein optionally include, by way of non-limiting examples, solvents, cosolvents, emulsifiers, fragrances, lubricants, gelling agents, thickeners, spreading agents, humectants, antioxidants, preservatives, including combinations thereof, known to the art.

Methods of Treatment Using Bath or Soak

In some embodiments, the compositions and formulations comprising glucosamine or a pharmaceutically acceptable salt thereof and adapted for use in a bath or soak are used for treatment of a subject in need thereof. In further embodiments, the subject is suffering from, by way of non-limiting examples, pain, inflammation, injury, and arthritis. In an particular embodiment, the subject is suffering from osteoarthritis.

In some embodiments, the methods of treatment comprise administering to the subject glucosamine or a pharmaceutically acceptable salt thereof by immersion in a bath or soak. In some embodiments, administration is, by way of non-limiting examples 1, 2, 3, 4, 5, 6, 7, 8 or more times a day. In some embodiments, administration is more than 1, 2, 3, 4, 5, 6, 7, or 8 times a day. In some embodiments, administration is 1 to 5 times a day, 1 to 3 times a day, or 1 to 2 times a day. In a particular embodiment, administration is once a day.

In some embodiments, treatment has a duration of, for example, 1, 2, 3, 4, 5, 6, 7, 8, 9, 10 or more days. In further embodiments, treatment has a duration of, for example, 1, 2, 3, 4, 5, 6, 7, 8, 9, 10, 11, 12 or more weeks. In still further embodiments, treatment has a duration of, for example, 1, 2, 3, 4, 5, 6, 7, 8, 9, 10, 11, 12 or more months. In some embodiments, treatment is chronic. In some embodiments, treatment has a duration of, for example, greater than 1 week, greater than 2 weeks, greater than 3 weeks, greater than 4 weeks, greater than 8 weeks, greater than 12 weeks, greater than 24 weeks. In some embodiments, treatment has a duration of, about 1 week to about 2 weeks, about 2 weeks to about 4 weeks, about 4 weeks to about 6 weeks, about 6 weeks to about 8 weeks, about 8 weeks to about 10 weeks, about 10 weeks to about 12 weeks, about 12 weeks to about 24 weeks, about 24 weeks to about 36 weeks, and the like. In a particular embodiment, a treatment regimen includes 1 to 3 treatments per day for 1 to 12 weeks.

In some embodiments, the methods of treatment further comprise administering to the subject oral medications or supplements as described further herein. In further embodiments, the methods of treatment comprise orally administering to the subject glucosamine or a pharmaceutically acceptable salt thereof, chondroitin or a pharmaceutically acceptable salt thereof, and/or methylsulfonylmethane in combination therapy with one or more of the transdermal and transmucosal glucosamine products described herein.

Lozenges

In some embodiments, described herein are lozenges comprising glucosamine or a pharmaceutically acceptable salt thereof, compositions and formulations adapted therefor, and methods of treatment using the same. A lozenge described herein is a small tablet intended to be held in the mouth and dissolve slowly to administer one or more medications and/or supplements. The lozenges described herein are suitably formed as tablets, capsules, dragees, or nonpareils. In some embodiments, the lozenges provide a transmucosal route of administration (i.e., diffusion through a mucous membrane such as the buccal mucosa) for glucosamine or a pharmaceutically acceptable salt thereof and, optionally, other medications or supplements. In some embodiments, the lozenges are suitable for sublingual or buccal administration of glucosamine or a pharmaceutically acceptable salt thereof and, optionally, other medications or supplements.

Compositions and Formulations for Lozenge

Disclosed herein, in some embodiments, are compositions and formulations comprising glucosamine or a pharmaceutically acceptable salt thereof adapted for sublingual or buccal administration. In further embodiments, the glucosamine or a pharmaceutically acceptable salt thereof is selected from glucosamine, N-acetylglucosamine, glucosamine sulfate, glucosamine hydrochloride, and combinations thereof.

A lozenge suitably has a wide range of dose amounts of glucosamine. In various embodiments, suitable dose amounts of glucosamine are about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and 5000 milligrams, including increments therein. In other various embodiments, suitable dose amounts of glucosamine are greater than 100, 500, 1000, 1500, 2000, 2500, 3000, 3500, and 4000 milligrams, including increments therein. In yet other various embodiments, suitable dose amounts of glucosamine are less than 4000, 3500, 3000, 2500, 2000, 1500, 1000, 500, and 100 milligrams, including increments therein. In some embodiments, the quantity of glucosamine per lozenge is between 300 and 500 milligrams, between 500 and 750 milligrams, between 750 and 1000 milligrams, between 1000 and 1250 milligrams, between 1250 and 1500 milligrams, between 1500 and 1750 milligrams, between 1750 and 2000 milligrams, between 2000 and 2250 milligrams, between 2250 and 2500 milligrams, between 2500 and 2750 milligrams, between 2750 and 3000 milligrams, between 3000 and 3250 milligrams, between 3250 and 3500 milligrams, between 3500 and 3750 milligrams, or between 3750 and 4000 milligrams. In various embodiments, the compositions and formulations adapted for sublingual or buccal administration and lozenges described herein comprise about 1%, 5%, 10%, 15%, 20%, 25%, 30%, 35%, 40%, 45%, 50%, 55%, 60%, 65%, 70%, 75%, 80%, 85%, or 90% w/w glucosamine, including increments therein. In some embodiments, the compositions and formulations adapted for sublingual or buccal administration and lozenges described herein comprise greater than 1%, 5%, 10%, 20%, 30%, 40%, 50%, 60%, 70%, 80%, or 90% w/w glucosamine, including increments therein. In further embodiments, the compositions and formulations adapted for sublingual or buccal administration and lozenges described herein comprise about 1% to about 10% w/w glucosamine, about 10% to about 20% w/w glucosamine, about 20% to about 30% w/w glucosamine, about 30% to about 40% w/w glucosamine, about 40% to about 50% w/w glucosamine, about 50% to about 60% w/w glucosamine, about 60% to about 70% w/w glucosamine, or about 70% to about 80% w/w glucosamine.

In some embodiments, the compositions comprising glucosamine or a pharmaceutically acceptable salt thereof and adapted for sublingual or buccal administration further comprise an additional medication or supplement. In further embodiments, the compositions comprise chondroitin or a pharmaceutically acceptable salt thereof, methylsulfonylmethane, or both.

A lozenge suitably has a wide range of dose amounts of chondroitin. In various embodiments, suitable dose amounts of chondroitin are about 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 or more milligrams, including increments therein. In a particular embodiment, the compositions comprising glucosamine or a pharmaceutically acceptable salt thereof adapted for sublingual or buccal administration further comprise about 100 to about 4000 milligrams of chondroitin per lozenge. In various embodiments, the compositions and formulations adapted for sublingual or buccal administration and lozenges described herein comprise about 1%, 5%, 10%, 15%, 20%, 25%, 30%, 35%, 40%, 45%, 50%, 55%, 60%, 65%, 70%, 75%, 80%, 85%, or 90% w/w chondroitin, including increments therein. In some embodiments, the compositions and formulations adapted for sublingual or buccal administration and lozenges described herein comprise greater than 1%, 5%, 10%, 20%, 30%, 40%, 50%, 60%, 70%, 80%, or 90% w/w chondroitin, including increments therein. In further embodiments, the compositions and formulations adapted for sublingual or buccal administration and lozenges described herein comprise about 1% to about 10% w/w chondroitin, about 10% to about 20% w/w chondroitin, about 20% to about 30% w/w chondroitin, about 30% to about 40% w/w chondroitin, about 40% to about 50% w/w chondroitin, about 50% to about 60% w/w chondroitin, or about 60% to about 70% w/w chondroitin.

A lozenge suitably has a wide range of dose amounts of methylsulfonylmethane. In various embodiments, suitable dose amounts of methylsulfonylmethane are about 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, and 7000 milligrams or more, including increments therein. In a particular embodiment, the compositions comprising glucosamine or a pharmaceutically acceptable salt thereof adapted for sublingual or buccal administration further comprise about 500 to about 6000 milligrams of methylsulfonylmethane per lozenge. In various embodiments, the compositions and formulations adapted for sublingual or buccal administration and lozenges described herein comprise about 1%, 5%, 10%, 15%, 20%, 25%, 30%, 35%, 40%, 45%, 50%, 55%, 60%, 65%, 70%, or 75% w/w methylsulfonylmethane, including increments therein. In some embodiments, the compositions and formulations adapted for sublingual or buccal administration and lozenges described herein comprise greater than 1%, 5%, 10%, 20%, 30%, 40%, 50%, 60%, or 70% w/w methylsulfonylmethane, including increments therein. In further embodiments, the compositions and formulations adapted for sublingual or buccal administration and lozenges described herein comprise about 1% to about 10% w/w methylsulfonylmethane, about 10% to about 20% w/w methylsulfonylmethane, about 20% to about 30% w/w methylsulfonylmethane, about 30% to about 40% w/w methylsulfonylmethane, about 40% to about 50% w/w methylsulfonylmethane, or about 60% to about 70% w/w methylsulfonylmethane.

In some embodiments, a lozenge is a hard, semi-hard, or soft candy lozenge made from sucrose and/or corn syrup or other melted hard, semi-hard, or soft candy bases. In some embodiments, a lozenge is a buffered formulation in order to aid in buccal absorption of one or more medications or supplements. In further embodiments, buffered formulations include sodium carbonate, sodium bicarbonate, sodium phosphate, calcium carbonate, magnesium hydroxide, potassium hydroxide, magnesium carbonate, aluminum hydroxide, and other substances known to those skilled in the art, as well as combinations thereof.

In some embodiments, a lozenge includes a sweetener, for example, aspartame, cyclamate, saccharin, stevia, sucralose, sorbitol, xylitol, and mannitol. In some embodiments, a lozenge includes a flavorant, for example, a candy taste, such as clove, cinnamon, chocolate, vanilla, orange, lemon, lime, cherry, strawberry, watermelon, and the like; essential oils such as peppermint, spearmint and the like; or other flavor. In some embodiments, a lozenge includes a fragrance, for example, a fruit, herb, floral, or other fragrance. In some embodiments, a lozenge includes a lubricant, for example, magnesium stearate and/or hydrogenated vegetable oil. In some embodiments, a lozenge is optionally colored with conventional, pharmaceutically acceptable food coloring agents. The lozenges described herein optionally contain a variety of other additives, which include, but are not limited to, preservatives, antimicrobial agents, and antioxidants.

Methods of Treatment Using Lozenge

In some embodiments, the compositions and formulations comprising glucosamine or a pharmaceutically acceptable salt thereof and adapted for use in a lozenge are used for treatment of a subject in need thereof. In further embodiments, the subject is suffering from, by way of non-limiting examples, pain, inflammation, injury, and arthritis. In an particular embodiment, the subject is suffering from osteoarthritis.

In some embodiments, the methods of treatment comprise administering to the subject glucosamine or a pharmaceutically acceptable salt thereof by a lozenge. In some embodiments, administration is, by way of non-limiting examples 1, 2, 3, 4, 5, 6, 7, 8, 9, 10, 11, 12, 13, 14, 15 or more times a day. In some embodiments, administration is more than 1, 2, 3, 4, 5, 6, 7, 8, 9, 10, 11, 12, 13, 14, or 15 times a day. In some embodiments, administration is 1 to 8 times a day, 1 to 6 times a day, or 1 to 3 times a day. In a particular embodiment, administration is 1 to 6 times a day.

In some embodiments, treatment has a duration of, for example, 1, 2, 3, 4, 5, 6, 7, 8, 9, 10 or more days. In further embodiments, treatment has a duration of, for example, 1, 2, 3, 4, 5, 6, 7, 8, 9, 10, 11, 12 or more weeks. In still further embodiments, treatment has a duration of, for example, 1, 2, 3, 4, 5, 6, 7, 8, 9, 10, 11, 12 or more months. In some embodiments, treatment is chronic. In some embodiments, treatment has a duration of, for example, greater than 1 week, greater than 2 weeks, greater than 3 weeks, greater than 4 weeks, greater than 8 weeks, greater than 12 weeks, greater than 24 weeks. In some embodiments, treatment has a duration of, about 1 week to about 2 weeks, about 2 weeks to about 4 weeks, about 4 weeks to about 6 weeks, about 6 weeks to about 8 weeks, about 8 weeks to about 10 weeks, about 10 weeks to about 12 weeks, about 12 weeks to about 24 weeks, about 24 weeks to about 36 weeks, and the like. In a particular embodiment, a treatment regimen includes 1 to 6 treatments per day for up to 1 month.

In some embodiments, the methods of treatment further comprise administering to the subject oral medications or supplements as described further herein. In further embodiments, the methods of treatment comprise orally administering to the subject glucosamine or a pharmaceutically acceptable salt thereof, chondroitin or a pharmaceutically acceptable salt thereof, and/or methylsulfonylmethane in combination therapy with one or more of the transdermal and transmucosal glucosamine products described herein.

Suppositories

In some embodiments, described herein are suppositories comprising glucosamine or a pharmaceutically acceptable salt thereof, compositions and formulations adapted therefor, and methods of treatment using the same. A suppository described herein is a small tablet or pellet intended to be inserted into the rectum (rectal suppository) or vagina (vaginal suppository) where it dissolves or melts to administer one or more medications and/or supplements. In some embodiments, the suppositories provide a transmucosal route of administration (i.e., diffusion through a mucous membrane such as the rectal or vaginal mucosa) for glucosamine or a pharmaceutically acceptable salt thereof and, optionally, other medications or supplements. In some embodiments, the suppositories are suitable for rectal or vaginal administration of glucosamine or a pharmaceutically acceptable salt thereof and, optionally, other medications or supplements.

Compositions and Formulations for Suppository

Disclosed herein, in some embodiments, are compositions and formulations comprising glucosamine or a pharmaceutically acceptable salt thereof adapted for rectal or vaginal administration. In further embodiments, the glucosamine or a pharmaceutically acceptable salt thereof is selected from glucosamine, N-acetylglucosamine, glucosamine sulfate, glucosamine hydrochloride, and combinations thereof.

A suppository suitably has a wide range of dose amounts of glucosamine. In various embodiments, suitable dose amounts of glucosamine are about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, and 3000 milligrams, including increments therein. In other various embodiments, suitable dose amounts of glucosamine are greater than 100, 500, 1000, 1500, 2000, 2500, and 3000 milligrams, including increments therein. In yet other various embodiments, suitable dose amounts of glucosamine are less than 3000, 2500, 2000, 1500, 1000, 500, and 100 milligrams, including increments therein. In some embodiments, the quantity of glucosamine per suppository is between 100 and 300 milligrams, between 300 and 500 milligrams, between 500 and 750 milligrams, between 750 and 1000 milligrams, between 1000 and 1250 milligrams, between 1250 and 1500 milligrams, between 1500 and 1750 milligrams, between 1750 and 2000 milligrams, between 2000 and 2250 milligrams, between 2250 and 2500 milligrams, between 2500 and 2750 milligrams, or between 2750 and 3000 milligrams. In various embodiments, the compositions and formulations adapted for rectal or vaginal administration and suppositories described herein comprise about 1%, 5%, 10%, 15%, 20%, 25%, 30%, 35%, 40%, 45%, 50%, 55%, 60%, 65%, 70%, 75%, 80%, 85%, or 90% w/w glucosamine, including increments therein. In some embodiments, the compositions and formulations adapted for rectal or vaginal administration and suppositories described herein comprise greater than 1%, 5%, 10%, 20%, 30%, 40%, 50%, 60%, 70%, 80%, or 90% w/w glucosamine, including increments therein. In further embodiments, the compositions and formulations adapted for rectal or vaginal administration and suppositories described herein comprise about 1% to about 10% w/w glucosamine, about 10% to about 20% w/w glucosamine, about 20% to about 30% w/w glucosamine, about 30% to about 40% w/w glucosamine, about 40% to about 50% w/w glucosamine, about 50% to about 60% w/w glucosamine, about 60% to about 70% w/w glucosamine, or about 70% to about 80% w/w glucosamine.

In some embodiments, the compositions comprising glucosamine or a pharmaceutically acceptable salt thereof and adapted for rectal or vaginal administration further comprise an additional medication or supplement. In further embodiments, the compositions comprise chondroitin or a pharmaceutically acceptable salt thereof, methylsulfonylmethane, or both.

A suppository suitably has a wide range of dose amounts of chondroitin. In various embodiments, suitable dose amounts of chondroitin are about 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 or more milligrams, including increments therein. In a particular embodiment, the compositions comprising glucosamine or a pharmaceutically acceptable salt thereof adapted for rectal or vaginal administration further comprise about 50 to about 2000 milligrams of chondroitin per suppository. In various embodiments, the compositions and formulations adapted for rectal or vaginal administration and suppositories described herein comprise about 1%, 5%, 10%, 15%, 20%, 25%, 30%, 35%, 40%, 45%, 50%, 55%, 60%, 65%, 70%, 75%, 80%, 85%, or 90% w/w chondroitin, including increments therein. In some embodiments, the compositions and formulations adapted for rectal or vaginal administration and suppositories described herein comprise greater than 1%, 5%, 10%, 20%, 30%, 40%, 50%, 60%, 70%, 80%, or 90% w/w chondroitin, including increments therein. In further embodiments, the compositions and formulations adapted for rectal or vaginal administration and suppositories described herein comprise about 1% to about 10% w/w chondroitin, about 10% to about 20% w/w chondroitin, about 20% to about 30% w/w chondroitin, about 30% to about 40% w/w chondroitin, about 40% to about 50% w/w chondroitin, about 50% to about 60% w/w chondroitin, or about 60% to about 70% w/w chondroitin.

A suppository suitably has a wide range of dose amounts of methylsulfonylmethane. In various embodiments, suitable dose amounts of methylsulfonylmethane are about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000 milligrams or more, including increments therein. In a particular embodiment, the compositions comprising glucosamine or a pharmaceutically acceptable salt thereof adapted for rectal or vaginal administration further comprise about 100 to about 5000 milligrams of methylsulfonylmethane per suppository. In various embodiments, the compositions and formulations adapted for rectal or vaginal administration and suppositories described herein comprise about 1%, 5%, 10%, 15%, 20%, 25%, 30%, 35%, 40%, 45%, 50%, 55%, 60%, 65%, 70%, or 75% w/w methylsulfonylmethane, including increments therein. In some embodiments, the compositions and formulations adapted for rectal or vaginal administration and suppositories described herein comprise greater than 1%, 5%, 10%, 20%, 30%, 40%, 50%, 60%, or 70% w/w methylsulfonylmethane, including increments therein. In further embodiments, the compositions and formulations adapted for rectal or vaginal administration and suppositories described herein comprise about 1% to about 10% w/w methylsulfonylmethane, about 10% to about 20% w/w methylsulfonylmethane, about 20% to about 30% w/w methylsulfonylmethane, about 30% to about 40% w/w methylsulfonylmethane, about 40% to about 50% w/w methylsulfonylmethane, or about 60% to about 70% w/w methylsulfonylmethane.

In some embodiments, the suppositories are made from a suppository base, such as hard fat. In further embodiments, a suppository base is an oily or fatty base. Conventional suppository bases are suitable including, by way of non-limiting examples, theobroma oil, hard fats, glycerides of fatty acids, glycerol-gelatin bases, and mixtures thereof. In still further embodiment, suitable hard fat bases include, but are not limited to, esterified mixtures of mono-, di- and triglycerides which are obtained by esterification of fatty acids. In some embodiments, the suppositories are made from a greasy base, such as cocoa butter, in which one or more medications or supplements and other excipients are dissolved. In further embodiments, a greasy base melts at body temperature. In other embodiments, the suppositories are made from a water soluble base, such as polyethylene glycol. In yet other embodiments, the suppositories are made of glycerol and gelatin. In some embodiments, a suppository includes a lubricant, for example, magnesium stearate and/or hydrogenated vegetable oil. The suppositories described herein optionally contain a variety of other additives, which include, but are not limited to, preservatives, antimicrobial agents, and antioxidants.

Methods of Treatment Using Suppository

In some embodiments, the compositions and formulations comprising glucosamine or a pharmaceutically acceptable salt thereof and adapted for use in a suppository are used for treatment of a subject in need thereof. In further embodiments, the subject is suffering from, by way of non-limiting examples, pain, inflammation, injury, and arthritis. In an particular embodiment, the subject is suffering from osteoarthritis.

In some embodiments, the methods of treatment comprise administering to the subject glucosamine or a pharmaceutically acceptable salt thereof by a suppository. In some embodiments, administration is, by way of non-limiting examples 1, 2, 3, 4, 5, 6, or more times a day. In some embodiments, administration is more than 1, 2, 3, 4, 5, or 6 times a day. In some embodiments, administration is 1 to 6 times a day, 1 to 3 times a day, or 1 to 2 times a day. In a particular embodiment, administration is 1 to 3 times a day.

In some embodiments, treatment has a duration of, for example, 1, 2, 3, 4, 5, 6, 7, 8, 9, 10 or more days. In further embodiments, treatment has a duration of, for example, 1, 2, 3, 4, 5, 6, 7, 8, 9, 10, 11, 12 or more weeks. In still further embodiments, treatment has a duration of, for example, 1, 2, 3, 4, 5, 6, 7, 8, 9, 10, 11, 12 or more months. In some embodiments, treatment is chronic. In some embodiments, treatment has a duration of, for example, greater than 1 week, greater than 2 weeks, greater than 3 weeks, greater than 4 weeks, greater than 8 weeks, greater than 12 weeks, greater than 24 weeks. In some embodiments, treatment has a duration of, about 1 week to about 2 weeks, about 2 weeks to about 4 weeks, about 4 weeks to about 6 weeks, about 6 weeks to about 8 weeks, about 8 weeks to about 10 weeks, about 10 weeks to about 12 weeks, about 12 weeks to about 24 weeks, about 24 weeks to about 36 weeks, and the like. In a particular embodiment, a treatment regimen includes 1 to 3 treatments per day for up to 1 month.

In some embodiments, the methods of treatment further comprise administering to the subject oral medications or supplements as described further herein. In further embodiments, the methods of treatment comprise orally administering to the subject glucosamine or a pharmaceutically acceptable salt thereof, chondroitin or a pharmaceutically acceptable salt thereof, and/or methylsulfonylmethane in combination therapy with one or more of the transdermal and transmucosal glucosamine products described herein.

Dermal Patches

In some embodiments, described herein are transdermal delivery patches (dermal patches) comprising glucosamine or a pharmaceutically acceptable salt thereof, compositions and formulations adapted therefor, and methods of treatment using the same. A dermal patch described herein is a medicated adhesive patch intended to be placed, directly and externally, on the skin to deliver a specific dose of one or more medications and/or supplements through the skin and into the bloodstream. In some embodiments, the dermal patches are suitable for topical administration of glucosamine or a pharmaceutically acceptable salt thereof and, optionally, other medications or supplements.

In some embodiments, the dermal patches provide a transdermal route of administration for glucosamine or a pharmaceutically acceptable salt thereof and, optionally, other medications or supplements. In further embodiments, a transdermal route of administration is a transcellular route wherein medications and/or supplements cross the skin by directly passing through both the phospholipids membranes and the cytoplasm of the dead keratinocytes that constitute the stratum corneum. In other embodiments, a transdermal route of administration is an intercellular route wherein medications and/or supplements cross the skin through the small spaces between the cells of the skin.

Many types of dermal patches are suitable for delivery of the compositions and formulations described herein. In various embodiments, suitable dermal patches include, by way of non-limiting examples, single-layer drug-in-adhesive patches, multi-layer drug-in-adhesive patches, reservoir (liquid compartment containing a drug solution or suspension) patches, and matrix (semi-solid matrix containing a solution or suspension) patches known to the art. In further embodiments, a suitable dermal patch comprises: a liner, which is removed prior to use; a solution or suspension in direct contact with release liner that contains one or more medications and/or supplements; an adhesive to adhere the components of the patch together and adhere the patch to a subject's skin; a membrane to controls the release of the medication and/or supplement (in reservoir and multi-layer patches); and a backing to protect the patch from the environment.

Compositions and Formulations for Dermal Patches

In some embodiments, the compositions for use with the dermal patches described herein comprise solutions or suspensions of glucosamine or a pharmaceutically acceptable salt thereof, and optionally, one or more other medications or supplements. In further embodiments, the composition is generally formulated in a dermatologically and/or cosmetically acceptable vehicle and/or carrier in a conventional manner well known in the cosmetic and pharmaceutical arts.

In some embodiments, the compositions for use with the dermal patches disclosed herein are formulated with one or more excipients suitable for providing a formulation comprising glucosamine or a pharmaceutically acceptable salt thereof, and optionally, one or more other medications or supplements. Suitable excipients include: emollients, such as *Carthamus tinctorius* (Safflower) seed oil and isononyl isononanoate; humectants/moisturizers/solvents, such as propylene glycol; spreading agents, such as diisopropyl adipate; surfactant systems, such as a combination of polysorbate 40 and sorbitan palmitate; skin conditioners, such as cyclopentasiloxane; emulsion stabilizers, such as cetearyl alcohol; rheological modifiers/thickeners, such as carbomer; antioxidants, such as tocopherol; pH adjusters, such as triethanolamine; and collating agents, such as disodium EDTA.

In some embodiments, the compositions for use with the dermal patches disclosed herein are formulated with one or more transdermal permeation enhancers for increasing absorption of the glucosamine or a pharmaceutically acceptable salt thereof, and optionally, one or more other medications or supplements. In further embodiments, a includes urea, a sulphoxide (e.g., dimethyl sulphoxide, etc.), an azone, an oxazolidinone (e.g., 4-decyloxazolidin-2-one, etc.), a pyrrolidone (e.g., N-methyl-2-pyrolidone, etc.), a fatty alcohol, a fatty acid ester (e.g., isopropyl linoleate, isopropyl palmitate, etc.), a fatty acid (e.g., lauric acid, myristic acid, capric acid, etc.), a fatty alcohol ether (e.g., EO-2-oleyl ether, EO-5-oleyl ether, etc.), a glycol (e.g., diethylene glycol, tetraethylene glycol, etc.), a surfactant (e.g., sodium lauryl sulfate, sodium oleate, etc.), an essential oil (e.g., eucalyptus, chenopodium, ylang-ylang, etc.), a terpene, or a terpenoid.

A composition or formulation for use with the dermal patches described herein suitably provides a wide range of dose amounts of glucosamine. In various embodiments, suitable dose amounts of glucosamine are about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, and 3000 milligrams per day, including increments therein. In other various embodiments, suitable dose amounts of glucosamine are greater than 100, 500, 1000, 1500, 2000, 2500, and 3000 milligrams per day, including increments therein. In yet other various embodiments, suitable dose amounts of glucosamine are less than 3000, 2500, 2000, 1500, 1000, 500, and 100 milligrams per day, including increments therein. In some embodiments, the quantity of glucosamine provided per day is between 100 and 300 milligrams, between 300 and 500 milligrams, between 500 and 750 milligrams, between 750 and 1000 milligrams, between 1000 and 1250 milligrams, between 1250 and 1500 milligrams, between 1500 and 1750 milligrams, between 1750 and 2000 milligrams, between 2000 and 2250 milligrams, between 2250 and 2500 milligrams, between 2500 and 2750 milligrams, or between 2750 and 3000 milligrams. In various embodiments, the compositions and formulations adapted for use with the dermal patches described herein comprise about 1%, 5%, 10%, 15%, 20%, 25%, 30%, 35%, 40%, 45%, 50%, 55%, 60%, 65%, 70%, 75%, 80%, 85%, or 90% w/w glucosamine, including increments therein. In some embodiments, the compositions and formulations adapted for use with the dermal patches described herein comprise greater than 1%, 5%, 10%, 20%, 30%, 40%, 50%, 60%, 70%, 80%, or 90% w/w glucosamine, including increments therein. In further embodiments, the compositions and formulations adapted for use with the dermal patches described herein comprise about 1% to about 10% w/w glucosamine, about 10% to about 20% w/w glucosamine, about 20% to about 30% w/w glucosamine, about 30% to about 40% w/w glucosamine, about 40% to about 50% w/w glucosamine, about 50% to about 60% w/w glucosamine, about 60% to about 70% w/w glucosamine, or about 70% to about 80% w/w glucosamine.

In some embodiments, the compositions comprising glucosamine or a pharmaceutically acceptable salt thereof and adapted for use with dermal patches further comprise an additional medication or supplement. In further embodiments, the compositions comprise chondroitin or a pharmaceutically acceptable salt thereof, methylsulfonylmethane, or both.

A composition or formulation for use with the dermal patches described herein suitably provides a wide range of dose amounts of chondroitin. In various embodiments, suitable dose amounts of chondroitin are about 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 or more milligrams per day, including increments therein. In a particular embodiment, the compositions comprising glucosamine or a pharmaceutically acceptable salt thereof adapted for use with the dermal patches described herein further comprise about 50 to about 2000 milligrams of chondroitin per patch. In various embodiments, the compositions and formulations adapted for use with the dermal patches described herein comprise about 1%, 5%, 10%, 15%, 20%, 25%, 30%, 35%, 40%, 45%, 50%, 55%, 60%, 65%, 70%, 75%, 80%, 85%, or 90% w/w chondroitin, including increments therein. In some embodiments, the compositions and formulations adapted for use with the dermal patches described herein comprise greater than 1%, 5%, 10%, 20%, 30%, 40%, 50%, 60%, 70%, 80%, or 90% w/w chondroitin, including increments therein. In further embodiments, the compositions and formulations adapted for use with the dermal patches described herein comprise about 1% to about 10% w/w chondroitin, about 10% to about 20% w/w chondroitin, about 20% to about 30% w/w chondroitin, about 30% to about 40% w/w chondroitin, about 40% to about 50% w/w chondroitin, about 50% to about 60% w/w chondroitin, or about 60% to about 70% w/w chondroitin.

A composition or formulation for use with the dermal patches described herein suitably provides a wide range of dose amounts of methylsulfonylmethane. In various embodiments, suitable dose amounts of methylsulfonylmethane are about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000 milligrams or more, including increments therein. In a particular embodiment, the compositions comprising glucosamine or a pharmaceutically acceptable salt thereof adapted for use with the dermal patches described herein further comprise about 200 to about 5000 milligrams of methylsulfonylmethane per patch. In various embodiments, the compositions and formulations adapted for use with the dermal patches described herein comprise about 1%, 5%, 10%, 15%, 20%, 25%, 30%, 35%, 40%, 45%, 50%, 55%, 60%, 65%, 70%, or 75% w/w methylsulfonylmethane, including increments therein. In some embodiments, the compositions and formulations adapted for use with the dermal patches described herein comprise greater than 1%, 5%, 10%, 20%, 30%, 40%, 50%, 60%, or 70% w/w methylsulfonylmethane, including increments therein. In further embodiments, the compositions and formulations adapted for use with the dermal patches described herein comprise about 1% to about 10% w/w methylsulfonylmethane, about 10% to about 20% w/w methylsulfonylmethane, about 20% to about 30% w/w methylsulfonylmethane, about 30% to about 40% w/w methylsulfonylmethane, about 40% to about 50% w/w methylsulfonylmethane, or about 60% to about 70% w/w methylsulfonylmethane.

Methods of Treatment Using Dermal Patches

In some embodiments, the compositions and formulations comprising glucosamine or a pharmaceutically acceptable salt thereof and adapted for use in a dermal patch are used for treatment of a subject in need thereof. In further embodiments, the subject is suffering from, by way of non-limiting examples, pain, inflammation, injury, and arthritis. In an particular embodiment, the subject is suffering from osteoarthritis.

In some embodiments, the methods of treatment comprise administering to the subject glucosamine or a pharmaceutically acceptable salt thereof by a transdermal delivery patch (dermal patch). In some embodiments, a dermal patch is applied, by way of non-limiting examples, three times a day, twice a day, once a day, once every two days, or once every three days, once every four days, once every five days, once every six days, or once a week. In some embodiments, administration is more than 1, 2, or 3 times a day. In some embodiments, administration is more than 1, 2, 3, 4, 5, 6, 7, or more times a week. In a particular embodiment, administration is once a day.

In some embodiments, treatment has a duration of, for example, 1, 2, 3, 4, 5, 6, 7, 8, 9, 10 or more days. In further embodiments, treatment has a duration of, for example, 1, 2, 3, 4, 5, 6, 7, 8, 9, 10, 11, 12 or more weeks. In still further embodiments, treatment has a duration of, for example, 1, 2, 3, 4, 5, 6, 7, 8, 9, 10, 11, 12 or more months. In some embodiments, treatment is chronic. In some embodiments, treatment has a duration of, for example, greater than 1 week, greater than 2 weeks, greater than 3 weeks, greater than 4 weeks, greater than 8 weeks, greater than 12 weeks, greater than 24 weeks. In some embodiments, treatment has a duration of, about 1 week to about 2 weeks, about 2 weeks to about 4 weeks, about 4 weeks to about 6 weeks, about 6 weeks to about 8 weeks, about 8 weeks to about 10 weeks, about 10 weeks to about 12 weeks, about 12 weeks to about 24 weeks, about 24 weeks to about 36 weeks, and the like. In a particular embodiment, a treatment regimen includes 1 treatment per day for up to 1 month.

In some embodiments, the methods of treatment further comprise administering to the subject oral medications or supplements as described further herein. In further embodiments, the methods of treatment comprise orally administering to the subject glucosamine or a pharmaceutically acceptable salt thereof, chondroitin or a pharmaceutically acceptable salt thereof, and/or methylsulfonylmethane in combination therapy with one or more of the transdermal and transmucosal glucosamine products described herein.

Topical Products

In some embodiments, described herein are topical products comprising glucosamine or a pharmaceutically acceptable salt thereof, compositions and formulations adapted therefor, and methods of treatment using the same. A topical product described herein is intended to be applied directly and externally to the skin to administer one or more medications and/or supplements. The topical products described herein are suitably formed as creams, lotions, gels, pastes, emulsions, salves, cleansers, toners, tonics, sprays, masques, sunscreens, and the like. In some embodiments, the topical products are suitable for topical administration of glucosamine or a pharmaceutically acceptable salt thereof and, optionally, other medications or supplements.

In some embodiments, the topical products provide a transdermal route of administration for glucosamine or a pharmaceutically acceptable salt thereof and, optionally, other medications or supplements. In further embodiments, a transdermal route of administration is a transcellular route wherein medications and/or supplements cross the skin by directly passing through both the phospholipids membranes and the cytoplasm of the dead keratinocytes that constitute the stratum corneum. In other embodiments, a transdermal route of administration is an intercellular route wherein medications and/or supplements cross the skin through the small spaces between the cells of the skin.

Compositions and Formulations for Topical Products

In some embodiments, the topical products described herein are formulated as a lotion or tonic, where they are either applied directly, or diluted with water and then applied. In other embodiments, the topical products are formulated as creams or ointments. In such formulations, glucosamine or a pharmaceutically acceptable salt thereof is added to a base moisturizer cream and mixed in with the base cream. For example, the compositions described herein are optionally added to sorbolene cream or other moisturisers. Alternatively, the compositions described herein are optionally added macadamia oil, jojoba oil, almond oil, or other nut and seed oils.

Suitable topical vehicles for use with the formulations of the topical products described herein are well known in the cosmetic and pharmaceutical areas and include water, lipid bases materials including oils and fats, soaps, surfactants, emollients, skin conditioning agents and emulsifying agents. In some cases, the choice of a suitable vehicle depends on the mode of delivery of the formulation. The active composition is generally incorporated in the dermatologically and/or cosmetically acceptable vehicle and/or carrier in a conventional manner well known in the cosmetic and pharmaceutical arts.

In some embodiments, the topical creams disclosed herein are formulated with one or more excipients suitable for providing a formulation comprising glucosamine or a pharmaceutically acceptable salt thereof, and optionally, one or more other medications or supplements. Suitable excipients include: emollients, such as *Carthamus tinctorius* (Safflower) seed oil and isononyl isononanoate; humectants/moisturizers/solvents, such as propylene glycol; spreading agents, such as diisopropyl adipate; surfactant systems, such as a combination of polysorbate 40 and sorbitan palmitate; skin conditioners, such as cyclopentasiloxane; emulsion stabilizers, such as cetearyl alcohol; rheological modifiers/thickeners, such as carbomer; antioxidants, such as tocopherol; pH adjusters, such as triethanolamine; and collating agents, such as disodium EDTA.

In some embodiments, the topical creams disclosed herein are formulated with one or more transdermal permeation enhancers for increasing absorption of the glucosamine or a pharmaceutically acceptable salt thereof, and optionally, one or more other medications or supplements. In further embodiments, a includes urea, a sulphoxide (e.g., dimethyl sulphoxide, etc.), an azone, an oxazolidinone (e.g., 4-decyloxazolidin-2-one, etc.), a pyrrolidone (e.g., N-methyl-2-pyrolidone, etc.), a fatty alcohol, a fatty acid ester (e.g., isopropyl linoleate, isopropyl palmitate, etc.), a fatty acid (e.g., lauric acid, myristic acid, capric acid, etc.), a fatty alcohol ether (e.g., EO-2-oleyl ether, EO-5-oleyl ether, etc.), a glycol (e.g., diethylene glycol, tetraethylene glycol, etc.), a surfactant (e.g., sodium lauryl sulfate, sodium oleate, etc.), an essential oil (e.g., eucalyptus, chenopodium, ylang-ylang, etc.), a terpene, or a terpenoid.

A topical product suitably has a wide range of concentrations of glucosamine. In various embodiments, suitable concentrations of glucosamine are about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 milligrams per gram, including increments therein. In other various embodiments, suitable concentrations of glucosamine are greater than 0.1, 0.5, 1.0, 2.0, 3.0, 4.0, 5.0, and 6.0 milligrams per gram, including increments therein. In yet other various embodiments, suitable concentrations of glucosamine are less than 7.0, 6.0, 5.0, 4.0, 3.0, 2.0, 1.0, and 0.5 milligrams per gram, including increments therein. In various embodiments, the compositions and formulations adapted for topical administration and topical products described herein comprise about 1%, 5%, 10%, 15%, 20%, 25%, 30%, 35%, 40%, 45%, 50%, 55%, 60%, 65%, 70%, 75%, 80%, 85%, or 90% w/w glucosamine, including increments therein. In some embodiments, the compositions and formulations adapted for topical administration and topical products described herein comprise greater than 1%, 5%, 10%, 20%, 30%, 40%, 50%, 60%, 70%, 80%, or 90% w/w glucosamine, including increments therein. In further embodiments, the compositions and formulations adapted for topical administration and topical products described herein comprise about 1% to about 10% w/w glucosamine, about 10% to about 20% w/w glucosamine, about 20% to about 30% w/w glucosamine, about 30% to about 40% w/w glucosamine, about 40% to about 50% w/w glucosamine, about 60% to about 70% w/w glucosamine, or about 70% to about 80% w/w glucosamine.

In some embodiments, the compositions comprising glucosamine or a pharmaceutically acceptable salt thereof and adapted for topical administration further comprise an additional medication or supplement. In further embodiments, the compositions comprise chondroitin or a pharmaceutically acceptable salt thereof, methylsulfonylmethane, or both.

A topical product suitably has a wide range of concentrations of chondroitin. In various embodiments, suitable concentrations of chondroitin are about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 milligrams per gram, including increments therein. In other various embodiments, suitable concentrations of chondroitin are greater than 0.1, 0.5, 1.0, 2.0, 3.0, 4.0, 5.0, and 6.0 milligrams per gram, including increments therein. In yet other various embodiments, suitable concentrations of chondroitin are less than 7.0, 6.0, 5.0, 4.0, 3.0, 2.0, 1.0, and 0.5 milligrams per gram, including increments therein. In various embodiments, the compositions and formulations adapted for topical administration and topical products described herein comprise about 1%, 5%, 10%, 15%, 20%, 25%, 30%, 35%, 40%, 45%, 50%, 55%, 60%, 65%, 70%, 75%, 80%, 85%, or 90% w/w chondroitin, including increments therein. In some embodiments, the compositions and formulations adapted for topical administration and topical products described herein comprise greater than 1%, 5%, 10%, 20%, 30%, 40%, 50%, 60%, 70%, 80%, or 90% w/w chondroitin, including increments therein. In further embodiments, the compositions and formulations adapted for topical administration and topical products described herein comprise about 1% to about 10% w/w chondroitin, about 10% to about 20% w/w chondroitin, about 20% to about 30% w/w chondroitin, about 30% to about 40% w/w chondroitin, about 40% to about 50% w/w chondroitin, about 50% to about 60% w/w chondroitin, or about 60% to about 70% w/w chondroitin.

A topical product suitably has a wide range of concentrations of methylsulfonylmethane. In various embodiments, suitable concentrations of methylsulfonylmethane are about 0.1, 0.5, 1, 2, 3, 4, 5, 6, 7, 8, 9, 10, 15, 20, 25, 30, 35, 40, 45, 50, 55, 60, 65, 70, and 75 milligrams per gram, including increments therein. In other various embodiments, suitable concentrations of methylsulfonylmethane are greater than 0.1, 0.5, 1, 2, 3, 4, 5, 6, 7, 8, 9, 10, 15, 20, 25, 30, 35, 40, 45, 50, 55, and 60 milligrams per gram, including increments therein. In yet other various embodiments, suitable concentrations of methylsulfonylmethane are less than 70, 65, 60, 55, 50, 45, 40, 35, 30, 25, 20, 15, 10, 9, 8, 7, 6, 5, 4, 3, 2, 1, and 0.5 milligrams per gram, including increments therein. In various embodiments, the compositions and formulations adapted for topical administration and topical products described herein comprise about 1%, 5%, 10%, 15%, 20%, 25%, 30%, 35%, 40%, 45%, 50%, 55%, 60%, 65%, 70%, or 75% w/w methylsulfonylmethane, including increments therein. In some embodiments, the compositions and formulations adapted for topical administration and topical products described herein comprise greater than 1%, 5%, 10%, 20%, 30%, 40%, 50%, 60%, or 70% w/w methylsulfonylmethane, including increments therein. In further embodiments, the compositions and formulations adapted for topical administration and topical products described herein comprise about 1% to about 10% w/w methylsulfonylmethane, about 10% to about 20% w/w methylsulfonylmethane, about 20% to about 30% w/w methylsulfonylmethane, about 30% to about 40% w/w methylsulfonylmethane, about 40% to about 50% w/w methylsulfonylmethane, or about 60% to about 70% w/w methylsulfonylmethane.

Methods of Treatment Using Topical Products

In some embodiments, the compositions and formulations comprising glucosamine or a pharmaceutically acceptable salt thereof and adapted for use in a topical product are used for treatment of a subject in need thereof. In further embodiments, the subject is suffering from, by way of non-limiting examples, pain, inflammation, injury, and arthritis. In an particular embodiment, the subject is suffering from osteoarthritis.

In some embodiments, the methods of treatment comprise topically administering to the subject glucosamine or a pharmaceutically acceptable salt thereof by a cream, lotion, gel, paste, emulsion, salve, tonic, spray, etc. In some embodiments, administration is, by way of non-limiting examples 1, 2, 3, 4, 5, 6, 7, 8, 9, 10 or more times a day. In some embodiments, administration is more than 1, 2, 3, 4, 5, 6, 7, or 8 times a day. In some embodiments, administration is 1 to 10 times a day, 1 to 5 times a day, or 1 to 3 times a day. In a particular embodiment, administration is 1 to 5 times a day.

In some embodiments, treatment has a duration of, for example, 1, 2, 3, 4, 5, 6, 7, 8, 9, 10 or more days. In further embodiments, treatment has a duration of, for example, 1, 2, 3, 4, 5, 6, 7, 8, 9, 10, 11, 12 or more weeks. In still further embodiments, treatment has a duration of, for example, 1, 2, 3, 4, 5, 6, 7, 8, 9, 10, 11, 12 or more months. In some embodiments, treatment is chronic. In some embodiments, treatment has a duration of, for example, greater than 1 week, greater than 2 weeks, greater than 3 weeks, greater than 4 weeks, greater than 8 weeks, greater than 12 weeks, greater than 24 weeks. In some embodiments, treatment has a duration of, about 1 week to about 2 weeks, about 2 weeks to about 4 weeks, about 4 weeks to about 6 weeks, about 6 weeks to about 8 weeks, about 8 weeks to about 10 weeks, about 10 weeks to about 12 weeks, about 12 weeks to about 24 weeks, about 24 weeks to about 36 weeks, and the like. In a particular embodiment, a treatment regimen includes 1 to 5 treatments per day for up to 1 month.

In some embodiments, the methods of treatment further comprise administering to the subject oral medications or supplements as described further herein. In further embodiments, the methods of treatment comprise orally administering to the subject glucosamine or a pharmaceutically acceptable salt thereof, chondroitin or a pharmaceutically acceptable salt thereof, and/or methylsulfonylmethane in combination therapy with one or more of the transdermal and transmucosal glucosamine products described herein.

Combination with Oral Pharmacotherapy

In various embodiments, the methods of treatment described herein include orally administering one or more of glucosamine or a pharmaceutically acceptable salt thereof, chondroitin or a pharmaceutically acceptable salt thereof, and methylsulfonylmethane to the subject in combination therapy with one or more of the transdermal and transmucosal glucosamine products (e.g., baths, soaks, lozenges, suppositories, patches, and topical creams) described herein.

In some embodiments, a subject is orally administered glucosamine, or a pharmaceutically acceptable salt thereof, in combination therapy with one or more of the transdermal and transmucosal glucosamine products described herein. In some embodiments, a subject is orally administered chondroitin, or a pharmaceutically acceptable salt thereof, in combination therapy with one or more of the transdermal and transmucosal glucosamine products described herein. In some embodiments, a subject is orally administered methylsulfonylmethane in combination therapy with one or more of the transdermal and transmucosal glucosamine products described herein. In further embodiments, a subject is orally administered glucosamine or a pharmaceutically acceptable salt thereof and chondroitin or a pharmaceutically acceptable salt thereof in combination therapy with one or more of the transdermal and transmucosal glucosamine products described herein. In further embodiments, a subject is orally administered glucosamine or a pharmaceutically acceptable salt thereof and methylsulfonylmethane in combination therapy with one or more of the transdermal and transmucosal glucosamine products described herein. In further embodiments, a subject is orally administered chondroitin or a pharmaceutically acceptable salt thereof and methylsulfonylmethane in combination therapy with one or more of the transdermal and transmucosal glucosamine products described herein. In still further embodiments, a subject is orally administered glucosamine or a pharmaceutically acceptable salt thereof, chondroitin or a pharmaceutically acceptable salt thereof, and methylsulfonylmethane in combination therapy with one or more of the transdermal and transmucosal glucosamine products described herein.

In some embodiments, the methods of treatment described herein include orally administering glucosamine or a pharmaceutically acceptable salt thereof to the subject. In further embodiments, glucosamine is orally administered as glucosamine sulfate and/or glucosamine hydrochloride. In some embodiments, glucosamine or a pharmaceutically acceptable salt thereof is administered in a dose of about 100 mg to about 4,000 mg per day. In further embodiments, glucosamine or a pharmaceutically acceptable salt thereof is administered in a dose of about 500 mg to about 2,000 mg per day. In various embodiments, a subject is orally administered about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, or 4000 mg of glucosamine per day, including increments therein. In a particular embodiment, a subject is orally administered glucosamine sulfate and/or glucosamine hydrochloride in a dose of 500 mg to 3,000 mg per day.

TABLE 5

Exemplary Oral Glucosamine Dosing

| Subject's Weight (lbs.) | Condition | Glucosamine Dosage |
|---|---|---|
| <100 | Hand pain, including osteoarthritis | 500 mg daily |
| 100-150 | | 1,000 mg daily |
| 150-200 | | 1,000 mg daily |
| 200-300 | | 1,500 mg daily |
| >300 | | 2,000 mg daily |
| <100 | Elbow pain, including osteoarthritis | 500 mg daily |
| 100-150 | | 1,000 mg daily |
| 150-200 | | 1,000 mg daily |
| 200-300 | | 2,000 mg daily |
| >300 | | 2,000 mg daily |
| <100 | Shoulder pain, including osteoarthritis | 1,500 mg daily |
| 100-150 | | 2,000 mg daily |
| 150-200 | | 2,500 mg daily |
| 200-300 | | 3,000 mg daily |
| >300 | | 3,000 mg daily |
| <100 | Knee pain, including osteoarthritis | 1,500 mg daily |
| 100-150 | | 3,000 mg daily |
| 150-200 | | 2,500 mg daily |
| 200-300 | | 3,000 mg daily |
| >300 | | 3,000 mg daily |
| <100 | Hip pain, including osteoarthritis | 2,500 mg daily |
| 100-150 | | 3,000 mg daily |
| 150-200 | | 3,000 mg daily |
| 200-300 | | 3,000 mg daily |
| >300 | | 3,000 mg daily |

TABLE 5-continued

Exemplary Oral Glucosamine Dosing

| Subject's Weight (lbs.) | Condition | Glucosamine Dosage |
|---|---|---|
| <100 | Lower back or neck pain, including osteoarthritis | 3,000 mg daily |
| 100-150 | | 3,000 mg daily |
| 150-200 | | 3,000 mg daily |
| 200-300 | | 3,000 mg daily |
| >300 | | 3,000 mg daily |
| <100 | Foot pain, including osteoarthritis | 500 mg daily |
| 100-150 | | 1,000 mg daily |
| 150-200 | | 1,500 mg daily |
| 200-300 | | 1,500 mg daily |
| >300 | | 2,000 mg daily |
| <100 | Toe pain, including osteoarthritis | 500 mg daily |
| 100-150 | | 500 mg daily |
| 150-200 | | 500 mg daily |
| 200-300 | | 1,000 mg daily |
| >300 | | 1,500 mg daily |

In some embodiments, the methods of treatment described herein include orally administering chondroitin to the subject. In further embodiments, chondroitin is orally administered as chondroitin sulfate. In some embodiments, chondroitin sulfate is administered in a dose of about 100 mg to about 2,500 mg per day. In further embodiments, chondroitin sulfate is administered in a dose of about 400 mg to about 1,200 mg per day. In various embodiments, a subject is orally administered about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, or 3500 mg of chondroitin per day, including increments therein. In a particular embodiment, a subject is orally administered chondroitin sulfate in a dose of 400 mg to 2,500 mg per day.

TABLE 6

Exemplary Oral Chondroitin Dosing

| Subject's Weight (lbs.) | Condition | Chondroitin Dosage |
|---|---|---|
| <100 | Hand pain, including osteoarthritis | 400 mg daily |
| 100-150 | | 800 mg daily |
| 150-200 | | 1,000 mg daily |
| 200-300 | | 1,200 mg daily |
| >300 | | 2,000 mg daily |
| <100 | Elbow pain, including osteoarthritis | 400 mg daily |
| 100-150 | | 800 mg daily |
| 150-200 | | 1,000 mg daily |
| 200-300 | | 1,500 mg daily |
| >300 | | 2,000 mg daily |
| <100 | Shoulder pain, including osteoarthritis | 800 mg daily |
| 100-150 | | 1,500 mg daily |
| 150-200 | | 2,000 mg daily |
| 200-300 | | 2,000 mg daily |
| >300 | | 2,500 mg daily |
| <100 | Knee pain, including osteoarthritis | 1,200 mg daily |
| 100-150 | | 1,800 mg daily |
| 150-200 | | 2,200 mg daily |
| 200-300 | | 2,500 mg daily |
| >300 | | 2,500 mg daily |
| <100 | Hip pain, including osteoarthritis | 2,000 mg daily |
| 100-150 | | 2,500 mg daily |
| 150-200 | | 2,500 mg daily |
| 200-300 | | 2,500 mg daily |
| >300 | | 2,500 mg daily |
| <100 | Lower back or neck pain, including osteoarthritis | 2,500 mg daily |
| 100-150 | | 2,500 mg daily |
| 150-200 | | 2,500 mg daily |
| 200-300 | | 2,500 mg daily |
| >300 | | 2,500 mg daily |
| <100 | Foot pain, including osteoarthritis | 400 mg daily |
| 100-150 | | 800 mg daily |
| 150-200 | | 1,200 mg daily |
| 200-300 | | 1,500 mg daily |
| >300 | | 2,000 mg daily |
| <100 | Toe pain, including osteoarthritis | 400 mg daily |
| 100-150 | | 800 mg daily |
| 150-200 | | 1,200 mg daily |
| 200-300 | | 1,500 mg daily |
| >300 | | 2,000 mg daily |

In some embodiments, the methods of treatment described herein include orally administering methylsulfonylmethane to the subject. In some embodiments, methylsulfonylmethane is administered in a dose of about 100 mg to about 10,000 mg per day. In further embodiments, methylsulfonylmethane is administered in a dose of about 500 mg to about 7,000 mg per day. In various embodiments, a subject is orally administered about 10, 20, 30, 40, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4500, 5000, 5500, 6000, 6500, 7000, 7500, 8000, 8500, 9000, 9500, 10000, 10500, 11000, 11500, 12000, 12500, 13000, 13500, or 14000 mg of methylsulfonylmethane per day, including increments therein.

EXAMPLES

The following examples illustrate representative embodiments and are not meant to be limiting.

Example 1

An 84-year-old female patient with a history of right total knee replacement and several year history of severe left knee osteoarthritis presents with constant pain that limits walking (e.g., uses a cane for ambulation). The patient has undergone ultrasound-guided steroid and hyaluronic injections, acupuncture, and physical therapy with little effect. Steroid injections offered moderate pain relief (~30-40% reduction) but the pain has returns after one week The patient is given glucosamine powder with instructions to use 1 kg in a bath soak every day for three days. (Directions: Fill the bath to the point where all of the powder dissolved—soak in bath for one hour.)

One week post treatment the patient reports 50% improvement, is able to walk for twice as long, and no loner requires a cane for outdoor ambulation. Three weeks post treatment the patient reports 70-75% improvement in pain and function. Although the patient continues to use a cane for outdoor ambulation she reports experiencing days with no pain at all. Two months post treatment the patient reports persistent 70-75% improvement in symptoms. Further results are shown in FIG. 1.

Example 2

Patients diagnosed with osteoarthritis were selected for an experimental study of a glucosamine bath soak as described herein. The patients were instructed to pour 1 kilogram of glucosamine powder into a hot bath and to sit in the hot bath for one hour. Patients were instructed to keep bath water as hot as they could without making themselves "too uncomfortable" and without burning themselves. Patients were instructed to repeat for five days (one bath per day), but patient 4 only completed 4 baths.

Prior to treatment, patients were surveyed for VAS pain scores and asked to list at least four activities that they cannot perform due to osteoarthritis and pain. Results are summarized below and in FIG. 2-8 (individual VAS scores) and 10 (data for Patients 1-7).

Patient 1 (Further treatment of same patient from Example 1)
Pre-treatment:
  VAS=9/10 on average
  Activity 1: I cannot walk normally
  Activity 2: I need a cane at home and don't want to need it
  Activity 3: I cannot walk without severe pain
  Activity 4: I cannot walk more than fifteen steps before having to sit down because of the pain
  Activity 5: I cannot carry anything
Post-Treatment:
  VAS=0/10 in the knee; 5/10 new pain in the back of the knee.
  Activity 1: I cannot walk normally
  Activity 2: I do not need a cane at home but do need it outside
  Activity 3: I can walk short distances without pain
  Activity 4: I can walk more than 30 steps before having to sit down because of the pain
  Activity 5: I cannot carry anything heavy while walking. I can carry very light objects.

Patient 2 (49 year old male with several year (>20) history of bilateral knee and shoulder pain that improves temporarily with steroid injections and acupuncture but returns within a few weeks).
Pre-treatment:
  VAS=4/10 (knee and shoulder pain)
  Activity 1: I can't roll over in bed without pain
  Activity 2: I can't walk up and down steps without knee pain
  Activity 3: I can't lift objects without pain in the lower back and knees
  Activity 4: I can't move arms around without shoulder pain
Post-Treatment:
  No difference reported after first day, but after second day, significant relief was noted.
  VAS=1/10
  Activity 1: I can't roll over in bed without pain because of lower back pain but the knee pain is fine
  Activity 2: I can walk up and down steps without knee pain
  Activity 3: I can lift objects without knee pain but I still have lower back pain
  Activity 4: I can move arms without shoulder pain Patient 3 (50 year old male with right big toe arthritis that was not helped with a steroid injection by his podiatrist nor with orthotics; pain present for about a year; recommended for surgery for the toe pain).
Pre-treatment
  VAS=9/10
  Activity 1: I can't run
  Activity 2: I can't walk without a limp
  Activity 3: I can't walk without pain
  Activity 4: I can't jump without pain
Post-Treatment
  VAS=2-3/10
  Activity 1: I can run
  Activity 2: I can walk without a limp
  Activity 3: I can walk without pain
  Activity 4: I can jump without pain
  Activity 5: I am going to play softball tonight for the first time in a long time.

Patient 4 (74 year old male with several year history of bilateral thumb osteoarthritis that has improved temporarily with steroid injections but has not improved with physical therapy, voltaren gel, or oral glucosamine).
Pre-treatment
  VAS=VAS=8/10
  Activity 1: I can't grip my golf club without pain
  Activity 2: I can't get through the day without them hurting like hell
  Activity 3: I can't fall asleep because of the pain
  Activity 4: I can't type without severe pain
Post-Treatment
  Four days post-treatment: VAS 8/10 (no change)
  Seven days post-treatment: VAS=4/10
  Activity 1: I can grip the golf club without pain
  Activity 2: I can get through the day without them hurting like hell
  Activity 3: I can fall asleep without the pain
  Activity 4: I can type without severe pain Patient 5 (57 year old male with severe right foot osteoarthritis recommended for major foot reconstruction surgery; steroid injections provide only temporary (days to weeks) relief; orthotics, physical therapy have not helped).
Pre-treatment
  VAS=5/10
  Activity 1: I can't walk without pain
  Activity 2: I can't run
  Activity 3: I can't jump
  Activity 4: I can't skateboard
10 Days Post-Treatment
  VAS=2/10
  Activity 1: I can walk without pain
  Activity 2: I can't run
  Activity 3: I can't jump
  Activity 4: I can't skateboard Patient 6 (74 year old obese male with several year history of severe right hip osteoarthritis who improves for about two weeks with fluoroscopically guided steroid injection and has not improved with physical therapy or chiropractic care; has been taking oral glucosamine with no relief; recommended for total hip replacement).
Pre-treatment
  VAS=7/10
  Activity 1: I can't take a walk down the block without my walker
  Activity 2: I can't walk fast
  Activity 3: I can't walk far
  Activity 4: I can't keep my balance too well Post-Treatment
VAS=5/10
Activity 1: I can take a walk down the block without my walker
Activity 2: I can't walk fast
Activity 3: I can walk around my house, which I could not do before.
Activity 4: I can't keep my balance too well.
Activity 5: I can clean my feet. I could not reach my feet before and now I can.

Patient states that he feels that the improvements he perceived were likely due to stretching while in the hot bath. He says he has not taken a hot bath in years.

Patient 7 (64 year old male with several year history of severe right knee osteoarthritis that improves temporarily with a steroid injection but has not responded to hyaluronic acid injections, physical therapy, or oral glucosamine; scheduled for total knee replacement).
Pre-treatment
VAS=9/10 on average
Activity 1: I can't walk
Activity 2: I can't get up off the ground without going onto all fours
Activity 3: I can't stand for more than 1-2 minutes before the pain becomes severe
Activity 4: I can't kneel at all
Activity 5: I cannot climb stairs, my knee locks 4-5 times per day
4 Days Post-Treatment
VAS=2-3/10
Activity 1: I can walk
Activity 2: I can get up off the ground without going on all fours
Activity 3: I stood all day today and did not think about it.
Activity 4: I can kneel
Activity 5: I can climb stairs, my knee locks 4-5 times per day
8 Days Post-Treatment
VAS=2-3/10
Activity 1: I can walk
Activity 2: I can get up off the ground without going on all fours
Activity 3: I stood all day today and did not think about it.
Activity 4: I can kneel
Activity 5: I can climb stairs
Activity 6: My knee locks 4-5 times per day Patient was amazed with reduction in pain but the knee continued to lock 4-5 times per day and so he elected to proceed with the total knee replacement.

Example 3

A 35 year old male (a former collegiate athlete who had ACL reconstruction at age 25 which resulted in low mobility and chronic arthritis, decades of running and sports which led to chronic, often disabling, back and neck pain (upper and lower), and also has general pains in the ankles, shins, and wrists, but continues to run and lift weights 3 times per week (total weekly mileage of 10-15 miles), relying on prophylactic agents (such as ibuprofen) and works 60-80 hours a week, travelling and sitting at a desk working on a laptop) was treated with a glucosamine bath soak as described herein for 5 days, using 1.5 kg glucosamine per daily bath for three days and then 1.0 kg glucosamine per daily bath for two days.

Figure 9A:
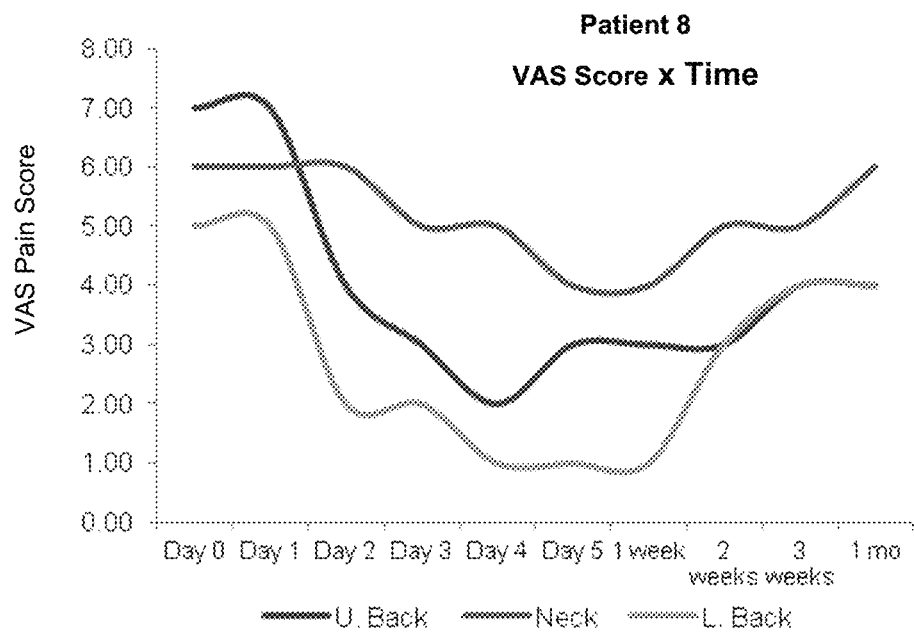
FIGS. 9A and 9B show the VAS score results of the treatment of a patient with a glucosamine bath soak as described herein in Example 3.
Figure 9B:
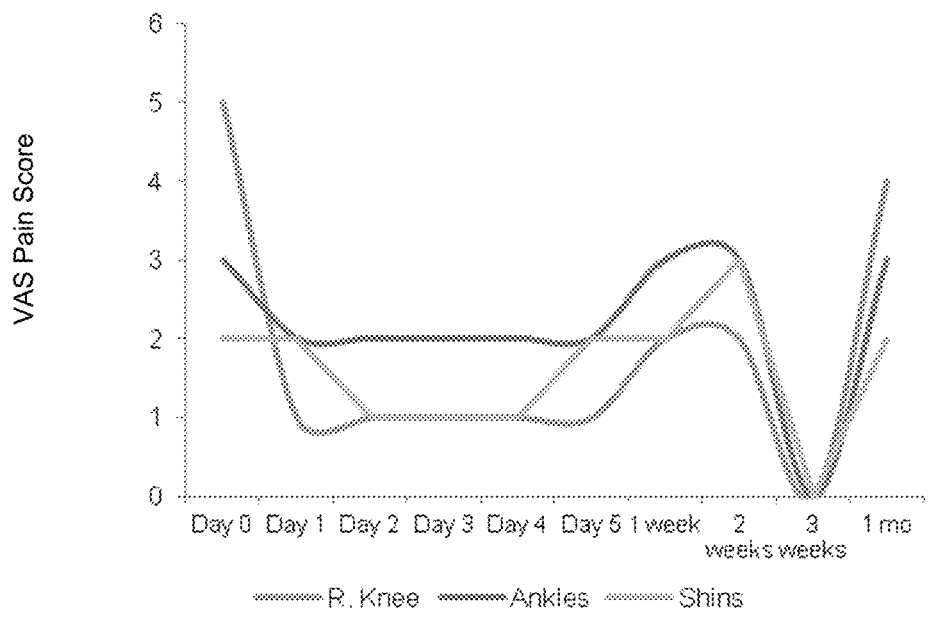
Figure 10:
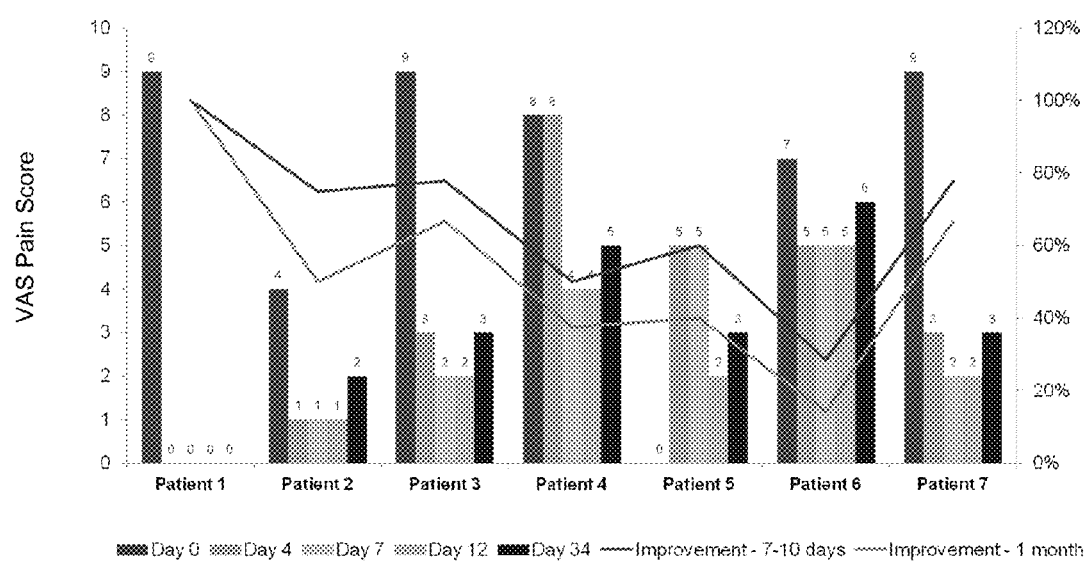
FIG. 10 shows the VAS score results from the treatment of a Patients 1-7 with a glucosamine bath soak as described herein in Example 2.

Pre-Treatment (May 18) VAS Scores:
Upper back: 7; Neck: 6; Lower Back: 5; Right Knee: 5; Ankles: 3; Shins: 2
Activity 1: I can not run two days in a row
Activity 2: I can not get comfortable on my back in bed
Activity 3: I am in pain when walking up stairs
Activity 4: I can not avoid at least one day of immobilizing pain in the neck & upper back
Results:
VAS Score results are shown in FIGS. 9A and 9B show that all improved in the following 3 weeks.
Activities: Able to run daily, sleep on back, and avoid immobilization; running times and distance ability was enhanced
Pain retuned in 4 week post 5th day of treatment While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of reducing pain in a subject comprising contacting a sufficient portion of the subject's external body with an aqueous solution comprising: glucosamine or a pharmaceutically acceptable salt thereof as the only active agent;
wherein said contacting is by immersion of said sufficient portion of the subject's external body in said aqueous solution for a period of time sufficient to allow absorption of the glucosamine, or a pharmaceutically acceptable salt thereof, by said subject to provide a reduction in pain.

2. The method of claim 1, wherein the glucosamine or a pharmaceutically acceptable salt thereof is selected from: glucosamine, N-acetylglucosamine, glucosamine sulfate, glucosamine hydrochloride, and combinations thereof.

3. A method of reducing pain in a subject comprising contacting a sufficient portion of the subject's external body with an aqueous solution comprising glucosamine or a pharmaceutically acceptable salt thereof and one or more of chondroitin sulfate and methylsulfonylmethane as the only active ingredients,
wherein said contacting is by immersion of said sufficient portion of the subject's external body in said aqueous solution for a period of time to provide a reduction in pain.

4. The method of claim 1, wherein the aqueous solution further comprises one or more selected from the group consisting of: sodium chloride, magnesium chloride, potassium chloride, and magnesium sulfate in an aqueous solution.

5. The method of claim 1, wherein the aqueous solution further comprises one or more transdermal permeation enhancer.

6. The method of claim 1, wherein the aqueous solution further comprises one or more transdermal permeation enhancer and one or more selected from the group consisting of sodium chloride, magnesium chloride, potassium chloride, and magnesium sulfate in an aqueous solution.

7. The method of claim 5, wherein the transdermal permeatin enhancer is one or more selected from the group consisting of: sea salt, urea, a sulphoxide, an azone, an oxazolidinone, a pyrrolidone, a fatty alcohol, a fatty acid ester, a fatty acid, a fatty alcohol ether, a surfactant, an essential oil, a terpene, and a terpenoid.

8. The method of claim 3, wherein the glucosamine or a pharmaceutically acceptable salt thereof is selected from: glucosamine, N-acetylglucosamine, glucosamine sulfate, glucosamine hydrochloride, and combinations thereof.

9. The method of claim 3, wherein the aqueous solution further comprises one or more selected from the group consisting of: sodium chloride, magnesium chloride, potassium chloride, and magnesium sulfate in an aqueous solution.

10. The method of claim 3, wherein the aqueous solution further comprises one or more transdermal permeation enhancer.

11. The method of claim 10, wherein the aqueous solution further comprises one or more selected from the group consisting of sodium chloride, magnesium chloride, potassium chloride, and magnesium sulfate in an aqueous solution.

12. The method of claim 9, wherein the transdermal permeation enhancer is one or more selected from the group consisting of: sea salt, urea, a sulphoxide, an azone, an oxazolidinone, a pyrrolidone, a fatty alcohol, a fatty acid ester, a fatty acid, a fatty alcohol ether, a surfactant, an essential oil, a terpene, and a terpenoid.

* * * * *